(12) United States Patent
Kanda et al.

(10) Patent No.: US 9,639,927 B2
(45) Date of Patent: May 2, 2017

(54) IMAGE PROCESSING APPARATUS, IMAGE PROCESSING METHOD, AND COMPUTER-READABLE RECORDING DEVICE

(71) Applicant: OLYMPUS CORPORATION, Tokyo (JP)

(72) Inventors: Yamato Kanda, Hino (JP); Makoto Kitamura, Hachioji (JP); Takashi Kono, Tachikawa (JP); Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 150 days.

(21) Appl. No.: 14/288,642

(22) Filed: May 28, 2014

(65) Prior Publication Data

US 2014/0270377 A1    Sep. 18, 2014

Related U.S. Application Data

(63) Continuation of application No. PCT/JP2012/080238, filed on Nov. 21, 2012.

(30) Foreign Application Priority Data

Nov. 30, 2011    (JP) .................... 2011-263091

(51) Int. Cl.
*G06K 9/00* (2006.01)
*G06T 7/00* (2017.01)
(Continued)

(52) U.S. Cl.
CPC .......... *G06T 7/0012* (2013.01); *A61B 1/0002* (2013.01); *A61B 1/00009* (2013.01);
(Continued)

(58) Field of Classification Search
None
See application file for complete search history.

(56) References Cited

U.S. PATENT DOCUMENTS 7,136,518 B2 * 11/2006 Griffin ................ A61B 5/0059
345/629
8,594,396 B2    11/2013 Matsuda et al.
(Continued)

FOREIGN PATENT DOCUMENTS

EP    2 085 019 A1    8/2009
EP    2 386 999 A2    11/2011
(Continued)

OTHER PUBLICATIONS

Extended Supplementary European Search Report dated Jul. 16, 2015 from related European Application No. 12 85 3575.4.
(Continued)

*Primary Examiner* — Weiwen Yang
(74) *Attorney, Agent, or Firm* — Scully, Scott, Murphy & Presser, P.C.

(57) ABSTRACT

An image processing apparatus includes an abnormal portion candidate region detection unit configured to detect a candidate region of an abnormal portion based on color information of each pixel constituting an image obtained by capturing an image of an inside of a lumen of a subject, a border neighboring pixel identifying unit configured to identify a border neighboring pixel which is a pixel existing in proximity to a border of the candidate region, a feature data calculation unit configured to calculate feature data based on a pixel value of the border neighboring pixel, and an abnormal portion region distinguishing unit configured to distinguish an abnormal portion region based on the feature data.

15 Claims, 20 Drawing Sheets

(51) Int. Cl.
| | |
|---|---|
| *G02B 23/24* | (2006.01) |
| *A61B 1/00* | (2006.01) |
| *G06K 9/46* | (2006.01) |
| *A61B 1/04* | (2006.01) |
| *G06T 7/11* | (2017.01) |
| *G06T 7/143* | (2017.01) |
| *G06T 7/155* | (2017.01) |
| *G06T 7/90* | (2017.01) |
| *G06T 7/136* | (2017.01) |

(52) U.S. Cl.
CPC .......... *A61B 1/041* (2013.01); *G02B 23/2484* (2013.01); *G06K 9/0014* (2013.01); *G06K 9/00147* (2013.01); *G06K 9/4604* (2013.01); *G06T 7/11* (2017.01); *G06T 7/136* (2017.01); *G06T 7/143* (2017.01); *G06T 7/155* (2017.01); *G06T 7/90* (2017.01); *G06K 9/4652* (2013.01); *G06T 2207/10024* (2013.01); *G06T 2207/10068* (2013.01); *G06T 2207/20041* (2013.01); *G06T 2207/20076* (2013.01); *G06T 2207/20152* (2013.01); *G06T 2207/30028* (2013.01); *G06T 2207/30096* (2013.01)

(56) References Cited

U.S. PATENT DOCUMENTS

| | | |
|---|---|---|
| 2010/0092055 A1 | 4/2010 | Matsuda |
| 2010/0208047 A1 | 8/2010 | Kitamura |
| 2010/0245552 A1* | 9/2010 | Higuchi ............. A61B 1/00096 348/68 |
| 2011/0311133 A1 | 12/2011 | Hirota et al. |

FOREIGN PATENT DOCUMENTS

| | | |
|---|---|---|
| JP | 2001-243479 A | 9/2001 |
| JP | 2005-192880 A | 7/2005 |
| JP | 2008-093172 A | 4/2008 |
| JP | 2008-307229 A | 12/2008 |
| JP | 2011-024628 A | 2/2011 |
| JP | 2011-234931 A | 11/2011 |
| WO | 2007/119297 A1 | 10/2007 |

OTHER PUBLICATIONS

Russ, J.C.,"The Image Processing Handbook", Chapter 8—"Processing Binary Images", Apr. 7, 2011, pp. 443-509.
International Search Report dated Feb. 26, 2013 issued in PCT/JP2012/080238.
Japanese Office Action dated Apr. 12, 2016 from related Japanese Patent Application No. 2011-263091, together with an English language translation.

* cited by examiner

IMAGE PROCESSING APPARATUS, IMAGE PROCESSING METHOD, AND COMPUTER-READABLE RECORDING DEVICE

CROSS-REFERENCE TO RELATED APPLICATIONS

This application is a continuation of PCT international application Ser. No. PCT/JP2012/080238 filed on Nov. 21, 2012 which designates the United States, incorporated herein by reference, and which claims the benefit of priority from Japanese Patent Application No. 2011-263091, filed on Nov. 30, 2011, incorporated herein by reference.

BACKGROUND OF THE INVENTION

1. Field of the Invention

The present invention relates to an image processing apparatus, an image processing method, and a computer-readable recording device for detecting an abnormal portion from an image obtained by capturing an image of an inside of a lumen of a subject.

2. Description of the Related Art

Conventionally, various methods have been studied to detect an abnormal portion from an intraluminal image obtained by capturing an image of an inside of a lumen of a subject using a medical observation apparatus such as an endoscope (which may be hereinafter simply referred to as image). For example, Japanese Laid-open Patent Publication No. 2005-192880 discloses an image processing method including mapping a pixel value of each pixel in an image into a feature space based on color information of each pixel, performing clustering in the feature space, thereafter, identifying a normal mucous membrane cluster and an abnormal portion cluster based on information on the size of each cluster, a center of gravity coordinate, and the like, and detecting a pixel, which belongs to the abnormal portion cluster, as an abnormal portion.

SUMMARY OF THE INVENTION

In some embodiments, an image processing apparatus includes an abnormal portion candidate region detection unit configured to detect a candidate region of an abnormal portion based on color information of each pixel constituting an image obtained by capturing an image of an inside of a lumen of a subject, a border neighboring pixel identifying unit configured to identify a border neighboring pixel which is a pixel existing in proximity to a border of the candidate region, a feature data calculation unit configured to calculate feature data based on a pixel value of the border neighboring pixel, and an abnormal portion region distinguishing unit configured to distinguish an abnormal portion region based on the feature data. The border neighboring pixel identifying unit includes a target border limiting unit configured to limit a border used for identifying the border neighboring pixel, to a part of an entire periphery of the border. The target border limiting unit includes an external side effective pixel identifying unit configured to identify an effective pixel which is a pixel in a region effective for calculation of the feature data, from an external side region which is in a specified range outwardly from a border pixel located at the border of the candidate region, and a corresponding border setting unit configured to set a border corresponding to the effective pixel.

In some embodiments, an image processing method includes detecting a candidate region of an abnormal portion based on color information of each pixel constituting an image obtained by capturing an image of an inside of a lumen of a subject, identifying a border neighboring pixel which is a pixel existing in proximity to a border of the candidate region, calculating feature data based on a pixel value of the border neighboring pixel, and distinguishing an abnormal portion region based on the feature data. The identifying of the border neighboring pixel includes limiting a border used for identifying the border neighboring pixel, to a part of an entire periphery of the border. The limiting of the border includes identifying an effective pixel which is a pixel in a region effective for calculation of the feature data, from an external side region which is in a specified range outwardly from a border pixel located at the border of the candidate region, and setting a border corresponding to the effective pixel.

In some embodiments, a computer-readable recording device is a recording device with an executable program stored thereon. The program instructs a processor to perform detecting a candidate region of an abnormal portion based on color information of each pixel constituting an image obtained by capturing an image of an inside of a lumen of a subject, identifying a border neighboring pixel which is a pixel existing in proximity to a border of the candidate region, calculating feature data based on a pixel value of the border neighboring pixel, and distinguishing an abnormal portion region based on the feature data. The identifying of the border neighboring pixel includes limiting a border used for identifying the border neighboring pixel, to a part of an entire periphery of the border. The limiting of the border includes identifying an effective pixel which is a pixel in a region effective for calculation of the feature data, from an external side region which is in a specified range outwardly from a border pixel located at the border of the candidate region, and setting a border corresponding to the effective pixel.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
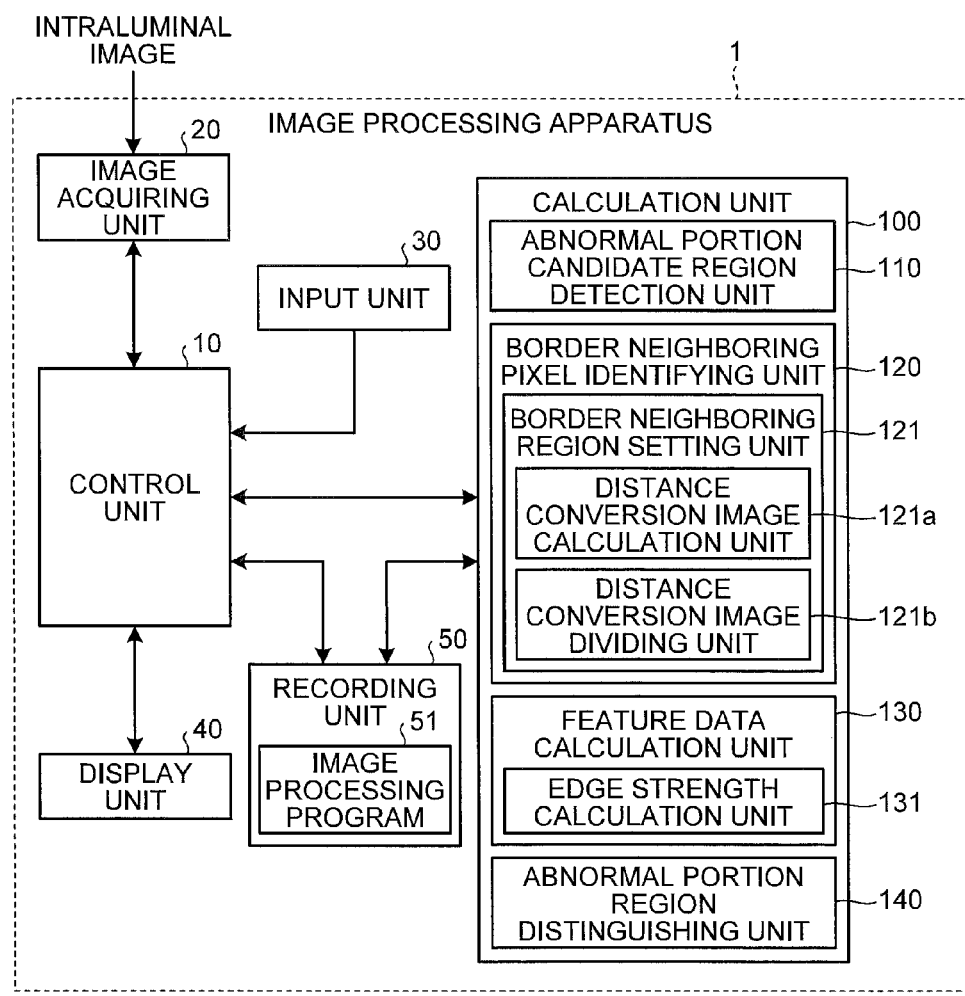
FIG. 1 is a block diagram illustrating a configuration of an image processing apparatus according to a first embodiment of the present invention.

Hereinafter, an image processing apparatus, an image processing method, and a computer-readable recording device according to embodiments of the present invention will be explained with reference to the drawings. It should be noted that the present invention is not limited by these embodiments. In the description of each drawing, the same portions are denoted with the same reference numerals.

In the embodiment explained below, for example, image processing for detecting a whitish affected portion (which may be hereinafter referred to as abnormal portion) from an intraluminal image obtained by causing a medical observation apparatus such as a capsule endoscope to capture inside of a lumen of a subject (which may be hereinafter simply referred to as image) will be explained. In the embodiments explained below, an intraluminal image which is target of image processing is a color image having a pixel level (pixel value) with regard to each color component (wavelength component) of R (red), G (green), B (blue) at each pixel position.

First Embodiment

FIG. 1 is a block diagram illustrating a configuration of an image processing apparatus according to a first embodiment of the present invention. The image processing apparatus 1 as illustrated in FIG. 1 includes a control unit 10 configured to control overall operation of the image processing apparatus 1, an image acquiring unit 20 configured to obtain image data corresponding to an image captured by a medical observation apparatus such as a capsule endoscope, an input unit 30 configured to receive an input signal which is input from the outside, a display unit 40 for performing various kinds of displays, a recording unit 50 configured to store various kinds of programs and image data obtained by the image acquiring unit 20, and a calculation unit 100 configured to execute specified image processing on image data.

The control unit 10 is achieved by hardware such as a CPU, and performs, e.g., transfer of data and command to each unit constituting the image processing apparatus 1 in accordance with an operation signal and the like which is input from the input unit 30 and image data which are input from the image acquiring unit 20 by reading various kinds of programs stored in the recording unit 50, thus centrally controlling overall operation of the image processing apparatus 1.

The image acquiring unit 20 is configured as necessary in accordance with a form of a system including a medical observation apparatus. For example, the medical observation apparatus is a capsule endoscope, and when a portable recording medium is used to exchange image data with the medical observation apparatus, the image acquiring unit 20 is constituted by a reader apparatus which detachably loads the recording medium and reads image data of an intraluminal image saved. When a server is installed to save image data of an intraluminal image captured by a medical observation apparatus, the image acquiring unit 20 is constituted by a communication apparatus and the like connected with a server, and obtains image data of an intraluminal image by performing data communication with the server. Alternatively, the image acquiring unit 20 may be constituted by an interface apparatus and the like for receiving an image signal via a cable from a medical observation apparatus such as an endoscope.

The input unit 30 is achieved with an input device, for example, a keyboard and a mouse, a touch panel, various kinds of switches, and the like, and outputs a received input signal to the control unit 10.

The display unit 40 is achieved with a display device such as an LCD and an EL display, and under the control of the control unit 10, the display unit 40 displays various kinds of screens including an intraluminal image.

The recording unit 50 is achieved with various kinds of IC memories such as a RAM and a ROM such as a flash memory capable of being updated and recorded, an internal hard disk or a hard disk connected with a data communication terminal, or an information recording device such as a CD-ROM and a reading apparatus therefor and the like. The recording unit 50 records not only image data of intraluminal images obtained by the image acquiring unit 20 but also, e.g., a program for causing the image processing apparatus 1 to operate and causing the image processing apparatus 1 to execute various kinds of functions, and data used during execution of the program. More specifically, the recording unit 50 not only records an image processing program 51 for causing the image processing apparatus 1 to execute image processing for detecting an abnormal portion from an intraluminal image but also records information such as color feature data of pixels which belong to whitish affected portions such as an aphthous ulcers and ulcer obtained by sampling in advance.

The calculation unit 100 is achieved with hardware such as a CPU, and reads the image processing program 51 to perform image processing on image data corresponding to an intraluminal image and perform various kinds of calculation processing for detecting an abnormal portion from an intraluminal image.

Next, the details of configuration of the calculation unit 100 will be explained.

As illustrated in FIG. 1, the calculation unit 100 includes an abnormal portion candidate region detection unit 110 configured to detect a candidate region of an abnormal portion based on color information of an intraluminal image, a border neighboring pixel identifying unit 120 configured to identify border neighboring pixels of the candidate region, a feature data calculation unit 130 configured to calculate feature data based on pixel values of the border neighboring pixels, and an abnormal portion region distinguishing unit 140 configured to distinguish an abnormal portion region based on the feature data.

Among them, the border neighboring pixel identifying unit 120 includes a border neighboring region setting unit 121 configured to set a border neighboring region of a candidate region, and identifies pixels in the border neighboring region as border neighboring pixels. In this case, the border neighboring region is a region having a width equal to or less than a specified width that is set at the inside and the outside of the candidate region across pixels (border pixels) located at the border of the candidate region. More specifically, the border neighboring region setting unit 121 includes a distance conversion image calculation unit 121a configured to calculate a distance conversion image representing a distance between a border pixel and each pixel in an image, and a distance conversion image dividing unit 121b configured to divide the distance conversion image into distance conversion regions respectively corresponding to the candidate regions.

The feature data calculation unit 130 includes an edge strength calculation unit 131 configured to calculate an edge strength of a border neighboring pixel, and is characterized by adopting the edge strength as the feature data.

Figure 2:
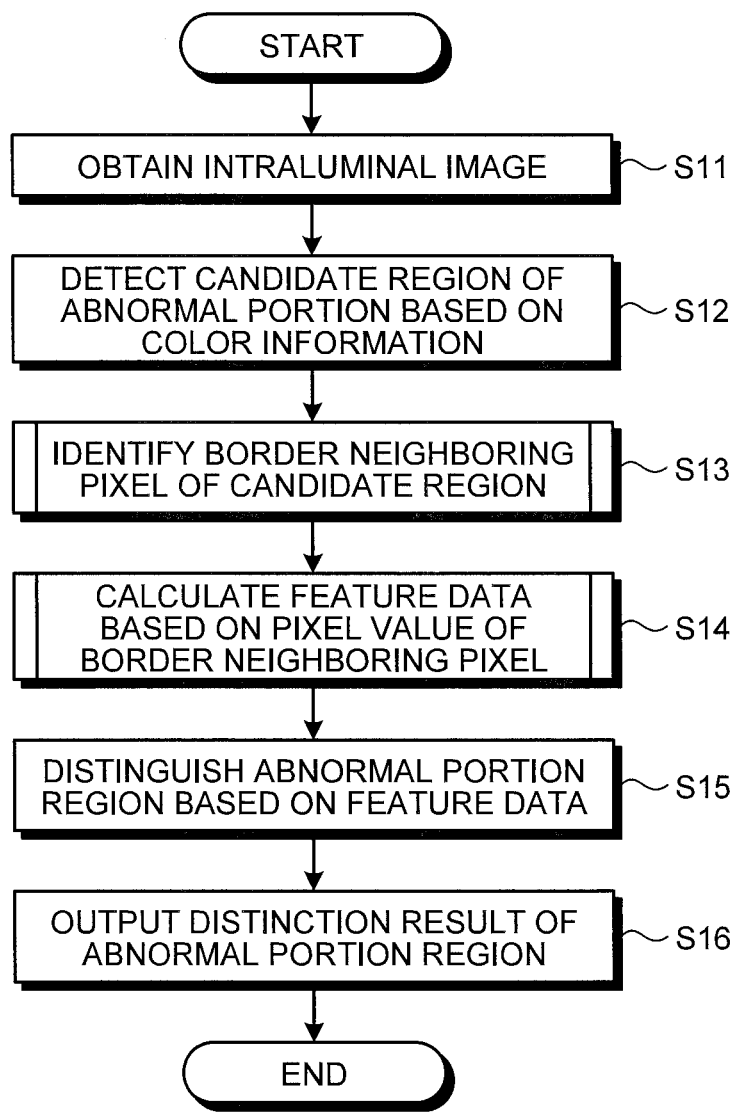
FIG. 2 is a flowchart illustrating operation of an image processing apparatus as illustrated in FIG. 1.
Figure 3:
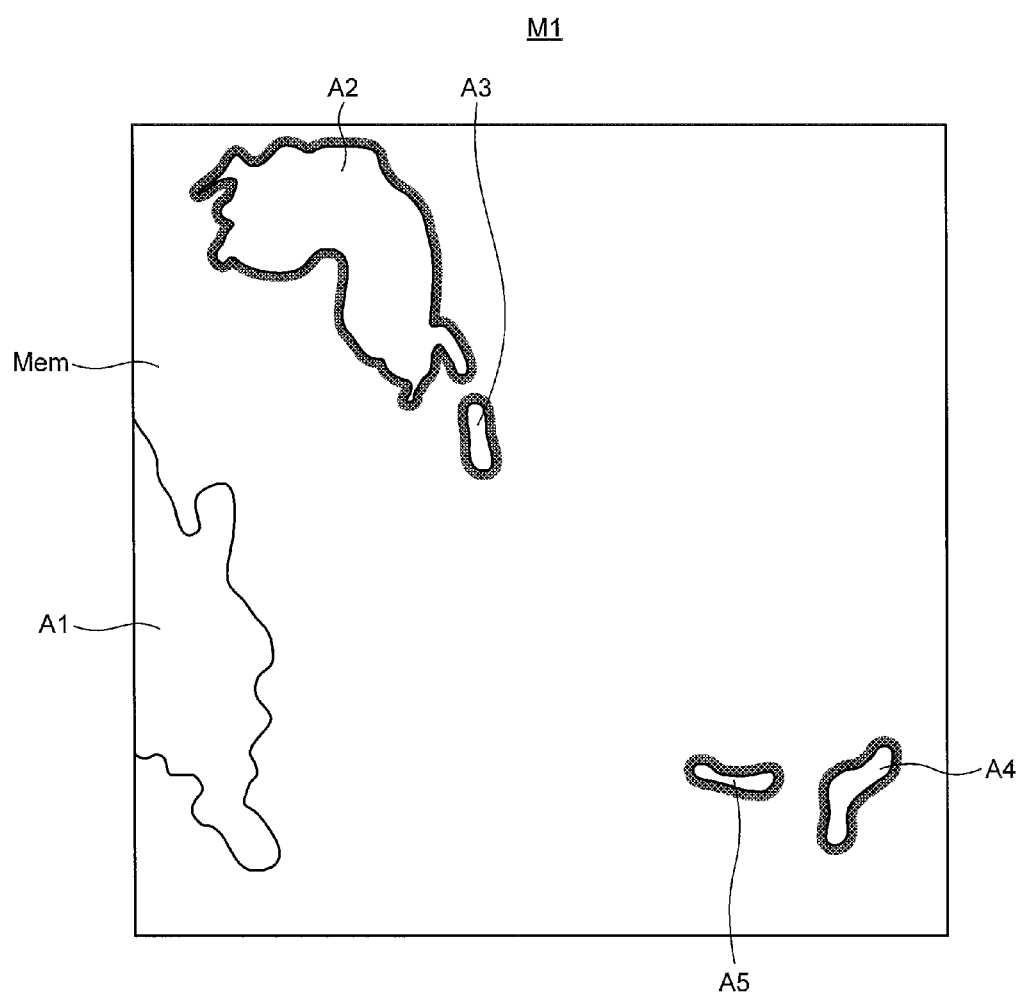
FIG. 3 is a schematic diagram illustrating an example of an image of processing target of the image processing apparatus as illustrated in FIG. 1.

Next, operation of the image processing apparatus 1 will be explained. FIG. 2 is a flowchart illustrating operation of the image processing apparatus 1. FIG. 3 is a schematic diagram illustrating an example of an image which is processing target of the image processing apparatus 1. As illustrated in FIG. 3, an image M1 includes a region A1 of a whitish affected portion which appears on a surface of a mucous membrane Mem, and regions A2 to A5 of residuals accumulated on (attached to) the surface of the mucous membrane Mem or floating in a space at a closer side with respect to the screen of the mucous membrane Mem. It should be noted that the regions A2 to A5 are protruding toward the closer side of the screen with respect to the mucous membrane Mem, and therefore, shades are drawn around the borders of the regions A2 to A5.

First, in step S11, the image acquiring unit 20 obtains an intraluminal image of a subject and stores the intraluminal image of the subject to the recording unit 50. The calculation unit 100 sequentially reads images of processing target (for example, image M1) from the recording unit 50.

In step S12, the abnormal portion candidate region detection unit 110 detects a candidate region of an abnormal portion based on the color information of each pixel constituting the image. In this case, abnormal portions such as aphthous ulcers and ulcer have whitish particular colors. Therefore, the abnormal portion candidate region detection unit 110 detects a region having whitish particular color from the image, and adopts this as a candidate region of an abnormal portion.

More specifically, the abnormal portion candidate region detection unit 110 performs the following calculation processing in advance using the color feature data of multiple pixels which belong to aphthous ulcers, ulcer, and the like recorded in the recording unit 50.

In this case, the color feature data mean pixel values of each of R, G, B components, or values calculated secondarily by a publicly known conversion based on the pixel values. Examples of the latter case include color difference calculated by YCbCr conversion, hue, chroma calculated by HSI conversion, color ratio such as G/R and B/G, and the like. The recording unit 50 records an average vector $\mu$ and a variance-covariance matrix Z given by the following expressions (1-1) and (1-2) based on feature vector $Fn=(fn\_1, fn\_2, \ldots, fn\_j, \ldots, fn\_k)^t$ composed of color feature data of pixels sampled in advance (fn_j denotes the j-th color feature data of the n-th sampled pixel, k denotes the number of feature data. It should be noted that "t" at the right hand side denotes a transposed vector).

$$\mu = \frac{1}{ND} \sum_{n=1}^{ND} Fn \tag{1-1}$$

$$Z = \frac{1}{ND} \sum_{n=1}^{ND} (Fn - \mu)(Fn - \mu)^t \tag{1-2}$$

In the expressions (1-1) and (1-2), ND denotes the number of sampled data. $(Fn-\mu)^t$ at the right hand side of the expression (1-2) denotes a transposed vector of the vector $(Fn-\mu)$.

The abnormal portion candidate region detection unit 110 generates feature vector $x=(x\_1, x\_2, \ldots, x\_j, \ldots, x\_k)^t$ composed of color feature data of each pixel in the image of the processing target (x_j denotes the j-th color feature data of the pixel). Then, the abnormal portion candidate region detection unit 110 calculates a determination index P (x) for determining whether each pixel is a particular color region in accordance with the following expression (1-3) based on the feature vector x, the average vector $\mu$, and the variance-covariance matrix Z recorded in the recording unit 50 in advance.

$$P(x) = \frac{1}{(2\pi)^{k/2} \times |Z|^{1/2}} \exp\left\{(x-\mu)^t \times \left(-\frac{1}{2}\right) Z^{-1} \times (x-\mu)\right\} \tag{1-3}$$

In the expression (1-3), $|Z|$ is a determinant of matrix Z, and $Z^{-1}$ is an inverse matrix of matrix Z. $(x-\mu)^t$ is a transposed vector of vector $(x-\mu)$.

Figure 4:
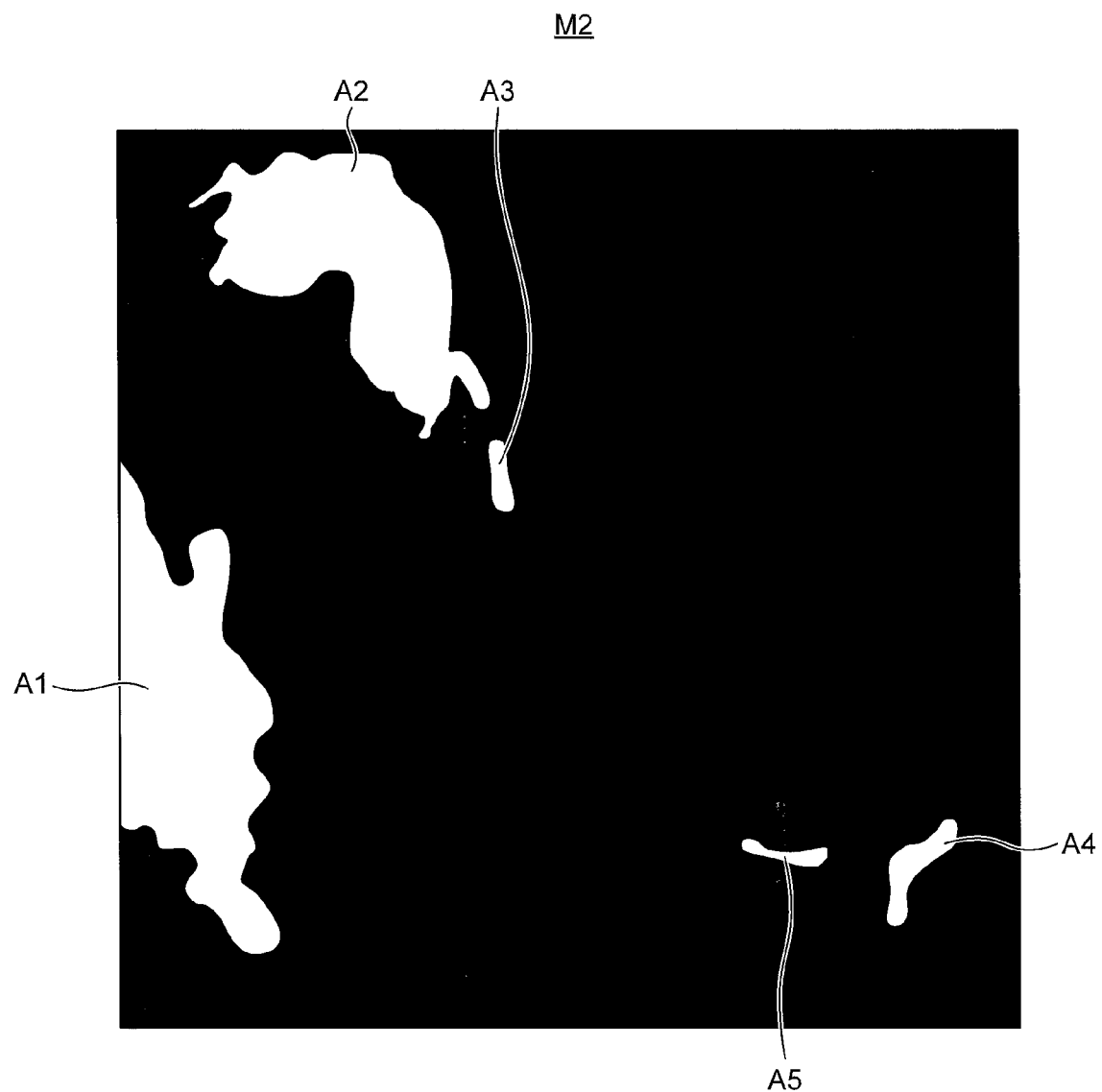
FIG. 4 is a schematic diagram illustrating a candidate region image corresponding to an image as illustrated in FIG. 3.

Thereafter, the abnormal portion candidate region detection unit 110 detects, as a candidate region, a pixel of which determination index P (x) is equal to or more than a specified threshold value. Then, a candidate region image is generated in which a value 1 is set for a pixel of a candidate region, and a value 0 is set for other pixels. FIG. 4 is a schematic diagram illustrating a candidate region image corresponding to the image M1 as illustrated in FIG. 3. As illustrated in FIG. 4, the regions A1 to A5 are shown in white in the image M2. These regions A1 to A5 are candidate regions of abnormal portions.

It should be noted that the detection method of a candidate region of an abnormal portion may be not only the detection method using the stochastic model explained above but also publicly-known various detection methods, for example, a method for setting a discrimination border in the feature space where the color feature data of each pixel is a component and a method for performing threshold value processing on a distance in a color feature space between color feature data of each pixel and representing color feature data such as lesion color (k-nearest neighbor algorithm. For reference, see JP 4266920 B1, CG-ARTS society "digital image processing", page 228 (NN method and kNN method)), and the like. Instead of detecting a candidate region using color feature data in units of pixels, an image is divided into multiple small regions based on, e.g., edge information in the image, and thereafter, a candidate region may be detected using color feature data in units of small regions.

Figure 5:
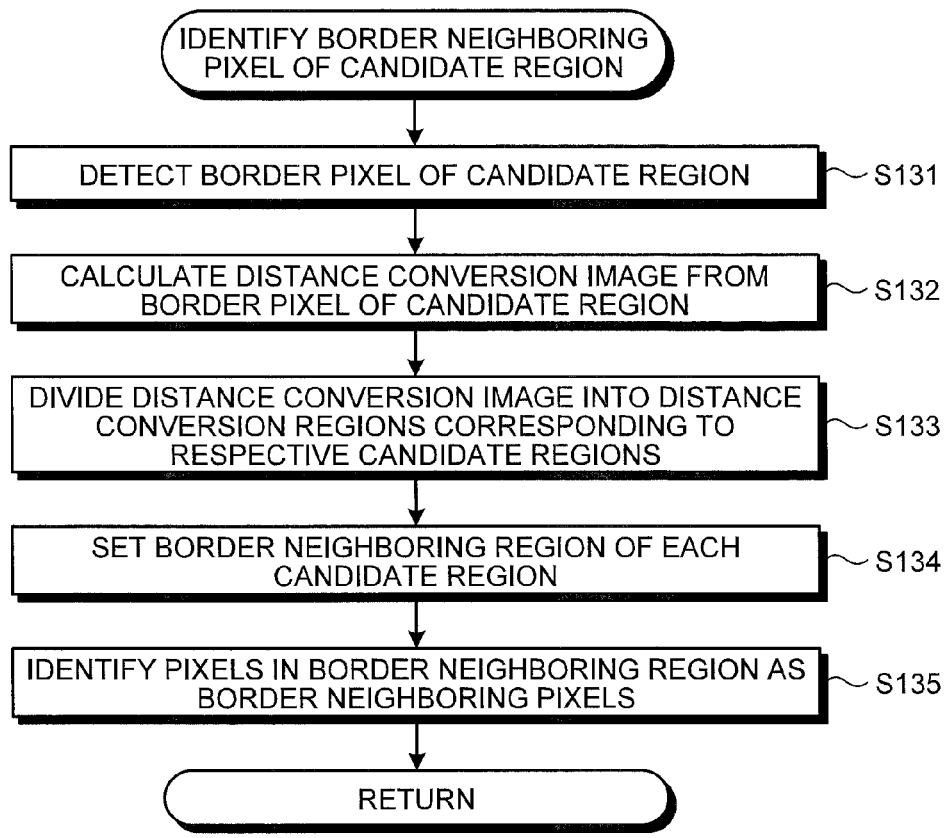
FIG. 5 is a flowchart illustrating operation of a border neighboring pixel identifying unit as illustrated in FIG. 1.

In step S13, the border neighboring pixel identifying unit 120 identifies a border neighboring pixel which is a pixel that exists in proximity to a border of a candidate region. FIG. 5 is a flowchart illustrating operation of the border neighboring pixel identifying unit 120 in detail.

Figure 6:
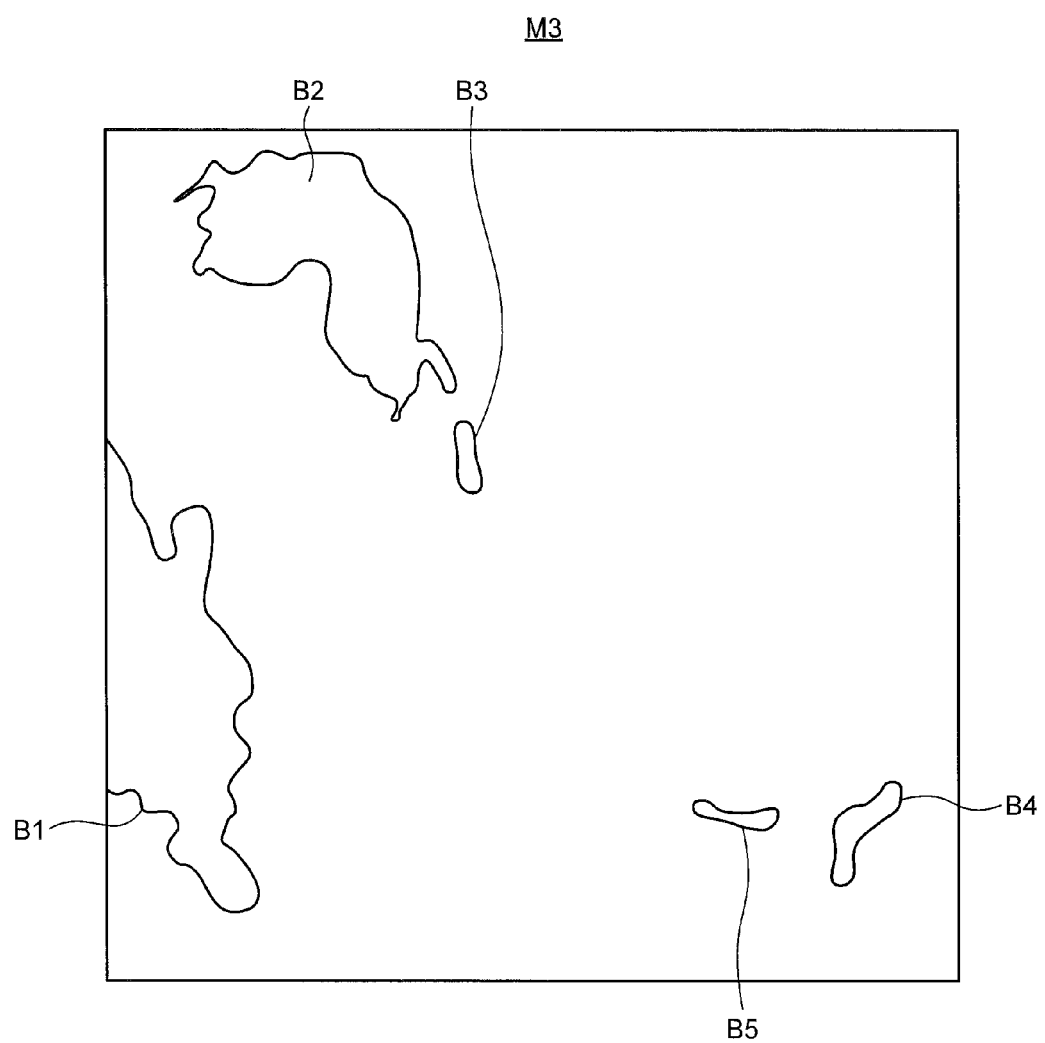
FIG. 6 is a schematic diagram illustrating border pixels detected from an image as illustrated in FIG. 4.

First, in step S131, the border neighboring pixel identifying unit 120 detects a border pixel of a candidate region. More specifically, while performing raster scan on an image including a candidate region, pixels of interest are set sequentially, and the pixel of interest is adopted as a border pixel in a case where the pixel of interest is a candidate region and any one of adjacent pixels is not the candidate region. Alternatively, in an image including a candidate region, a border pixel may be detected by performing publicly-known contour tracing (for reference, see, CG-ARTS society, "digital image processing", page 178 (contour tracing)). FIG. 6 is a schematic diagram illustrating border pixels detected from the image M2 as illustrated in FIG. 4. As illustrated in FIG. 6, the image M3 shows border pixel groups B1 to B5 corresponding to the candidate regions A1 to A5, respectively.

Figure 7:
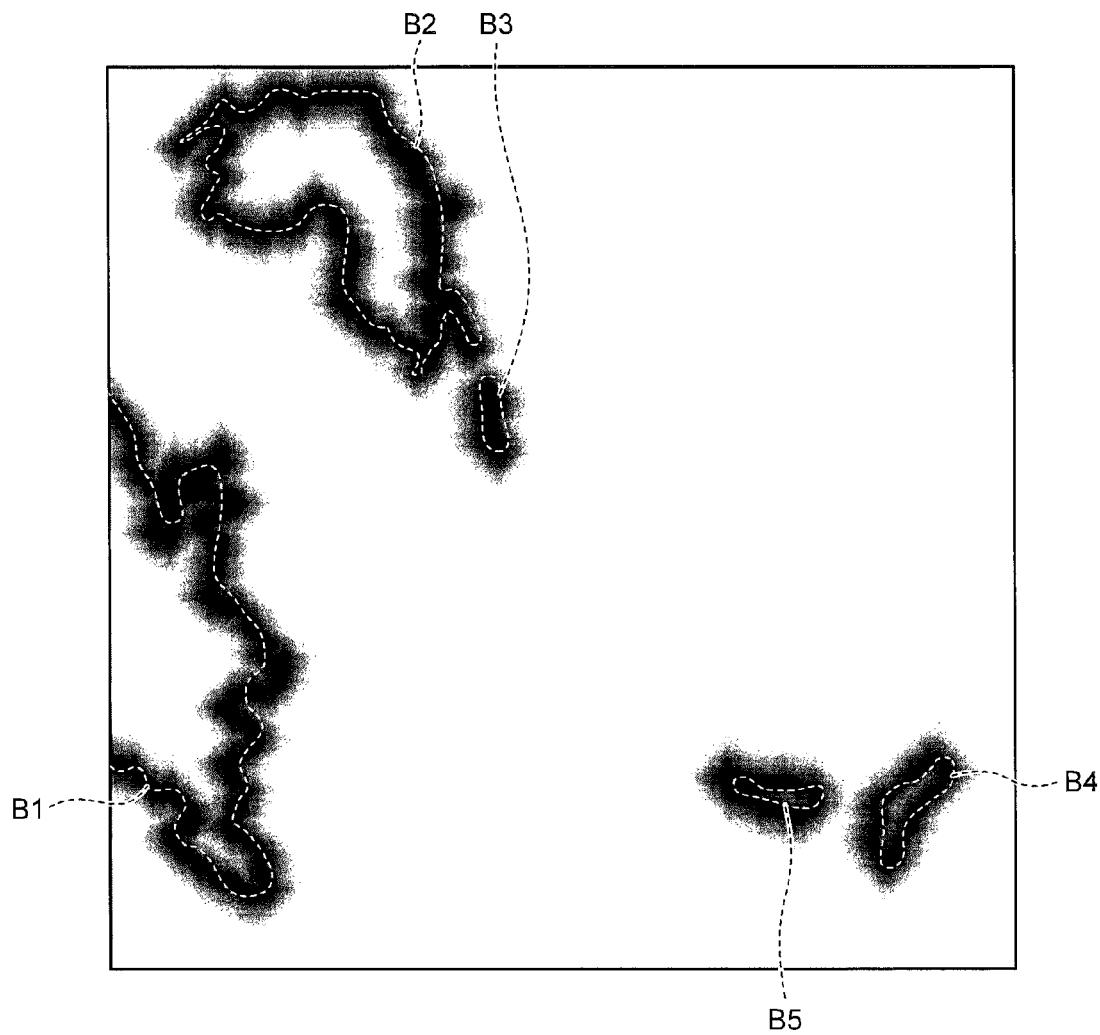
FIG. 7 is a schematic diagram illustrating d distance conversion image calculated from an image as illustrated in FIG. 6.

In step S132, the distance conversion image calculation unit 121a calculates a distance conversion image representing a distance between a border pixel of candidate regions and each pixel in an image. This can be realized by performing publicly-known distance conversion processing (for reference, see University of Tokyo Press, "image analysis handbook", page 576 (distance conversion and skeleton extraction)). FIG. 7 is a schematic diagram illustrating a distance conversion image calculated from the image M3 as illustrated in FIG. 6. As illustrated in FIG. 7, the pixel value (brightness) of each pixel in the image M4 is configured to be higher as the pixel is away from the border pixel groups B1 to B5.

In step S133, the distance conversion image dividing unit 121b divides the distance conversion image into distance conversion regions corresponding to the respective candidate regions. In this case, where there are multiple candidate regions in the image, the distance conversion image is divided in such a manner that the ridge of the pixel value is adopted as a border, so that the image can be divided into distance conversion regions corresponding to candidate regions.

Figure 8:
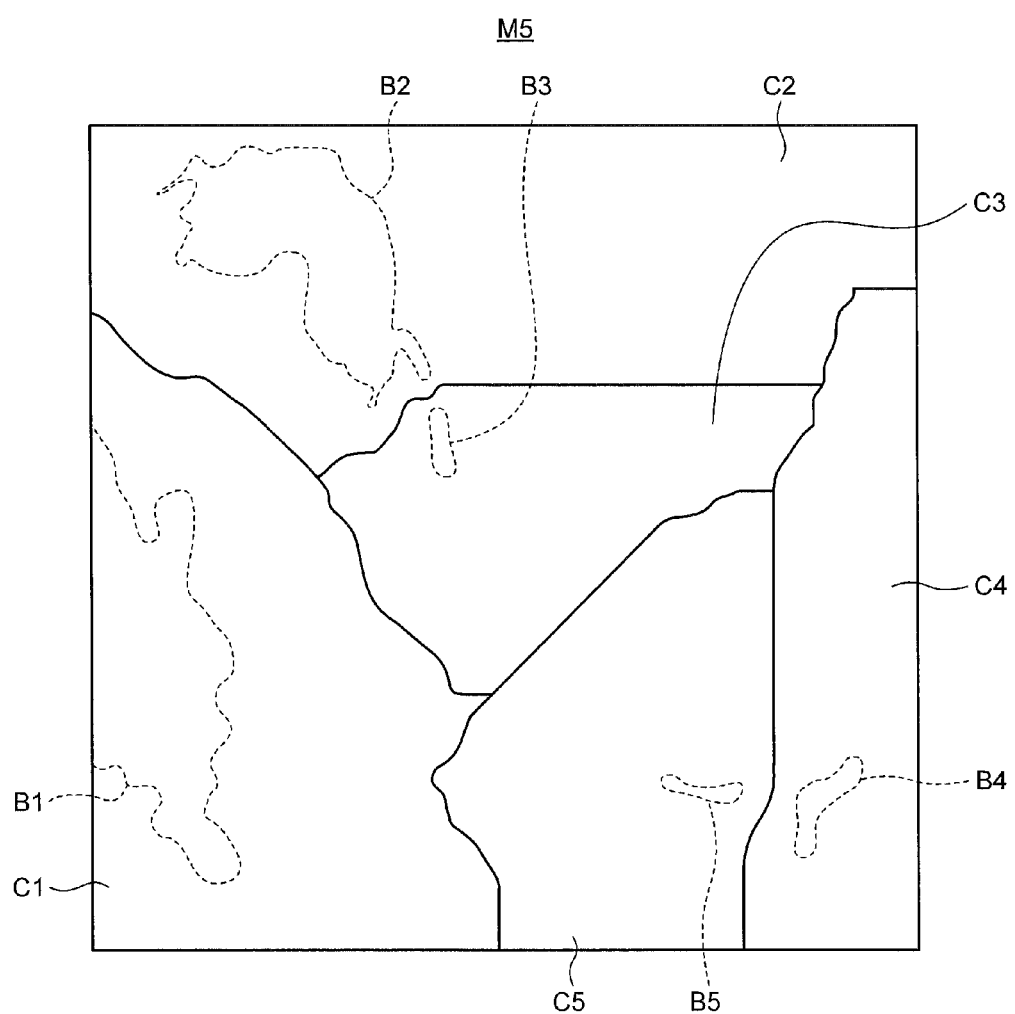
FIG. 8 is a schematic diagram illustrating a region label image obtained by dividing the image as illustrated in FIG. 7 into distance conversion regions.

The dividing of the image with the ridge of a pixel value being adopted as a border is done, for example, as follows. First, a gradient direction of the pixel value of each pixel is derived. At this occasion, the gradient direction is taken in such direction that the pixel value decreases. Next, the minimum value pixel that is attained when each pixel moves in the gradient direction of the pixel value is derived, and the image is divided in such a way that the pixels that attain the minimum value pixel and that are adjacent to each other are in the same region. After dividing, a label value for distinguishing each region is set in the pixels in each region, and a region label image is obtained. The image dividing method with the ridge of a pixel value being adopted as a border is disclosed in details in WO 2006/080239 by the inventor of the present application. FIG. 8 is a schematic diagram illustrating a region label image in which the image M4 as illustrated in FIG. 7 is divided into distance conversion regions. As illustrated in FIG. 8, the image M5 shows distance conversion regions C1 to C5 corresponding to candidate regions A1 to A5 as illustrated in FIG. 4.

Another method for dividing the distance conversion image may be watershed algorithm (for reference, see Luc Vincent and Pierre Soille. "Watersheds in digital spaces: An efficient algorithm based on immersion simulations", IEEE Transactions on Pattern Analysis and Machine Intelligence, Vol. 13, No. 6, pp. 583-598, June 1991). The watershed algorithm is a method for dividing an image as if a border is made between waters accumulated in different ditches when water is filled into a topography in which the pixel value information of an image is deemed as an altitude. Substantially the same image division result as the method disclosed in WO 2006/080239 can be obtained by executing the watershed algorithm on the distance conversion image.

Figure 9:
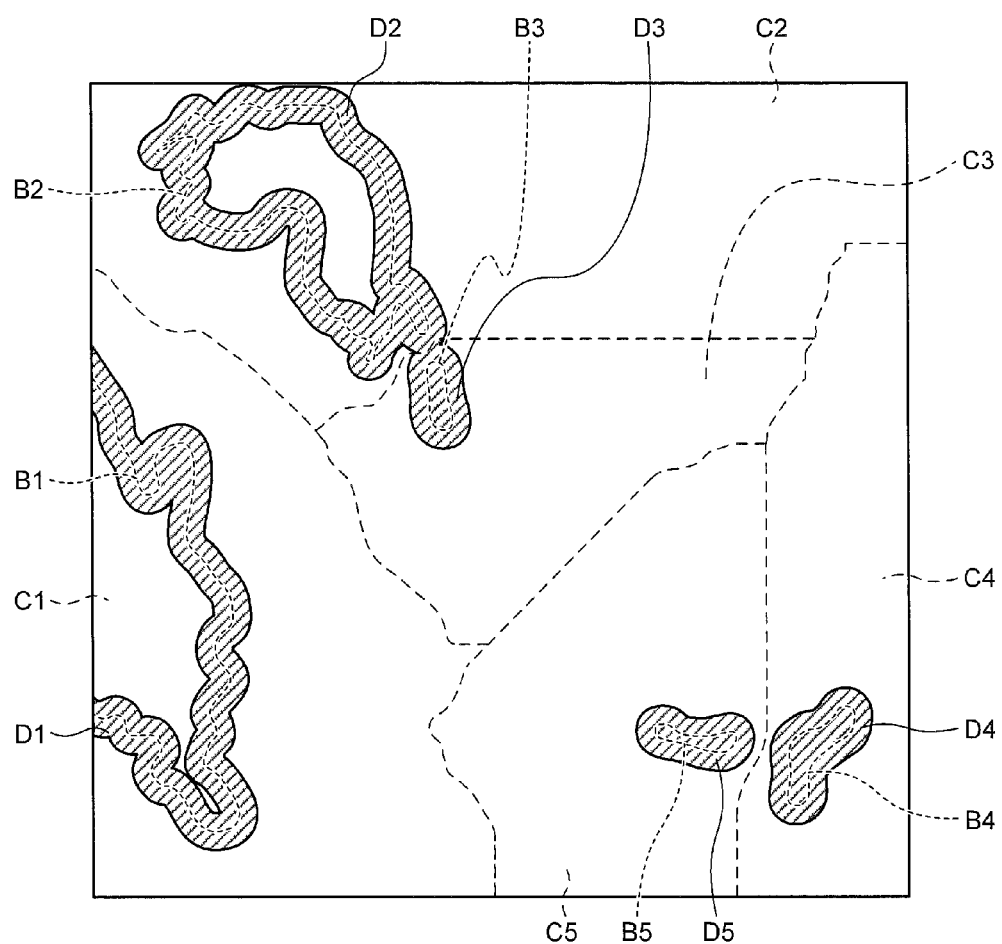
FIG. 9 is a schematic diagram illustrating border neighboring regions which are set based on the image as illustrated in FIG. 7.

In step S134, the border neighboring region setting unit 121 sets a border neighboring region of each candidate region. More specifically, the border neighboring region setting unit 121 determines that a pixel region having pixel values equal to or less than a specified value, i.e., a region where the distance from border pixels is equal to or less than a specified value, in a distance conversion region corresponding to each candidate region, is a border neighboring region of each candidate region. FIG. 9 is a schematic diagram illustrating a border neighboring region that is set based on the image M5 as illustrated in FIG. 8. As illustrated in FIG. 9, the distance conversion regions C1 to C5 of the image M6 indicate border neighboring regions D1 to D5 corresponding to border pixel groups B1 to B5.

Further, in step S135, the border neighboring pixel identifying unit 120 identifies pixels in the border neighboring region as border neighboring pixels. Thereafter, the processing in the main routine is performed back again.

Figure 10:
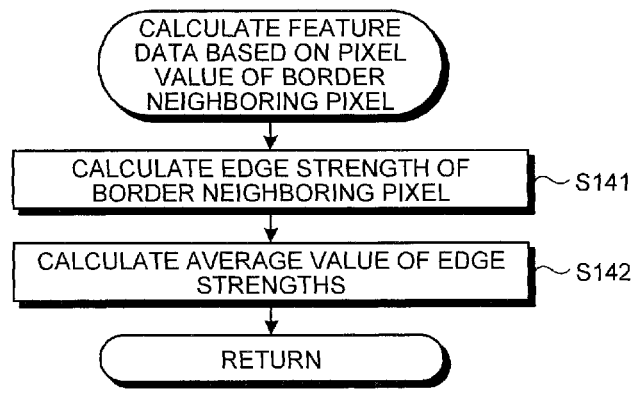
FIG. 10 is a flowchart illustrating calculation processing of feature data based on pixel values of the border neighboring pixels as illustrated in FIG. 1.

In step S14, the feature data calculation unit 130 calculates feature data based on pixel values of border neighboring pixels. FIG. 10 is a flowchart illustrating operation of the feature data calculation unit 130 in details.

First, In step S141, the edge strength calculation unit 131 calculates edge strengths of the border neighboring pixels. This can be achieved by applying a publicly-known first derivative filter (for reference, see CG-ARTS society "digital image processing", page 114 (derivative filter)) on pixel values of each wavelength component (R, G, B) in border neighboring pixels, thus calculating first derivative values of each pixel. At this occasion, in order to alleviate the influence caused by noises, for example, Sobel filter and the like which is a first derivative with smoothing may be applied.

In step S142, the feature data calculation unit 130 calculates an average value of edge strengths for each border neighboring region. In step S141, the edge strength is calculated for each wavelength component, and therefore, three average values corresponding to R, G, B wavelength components are obtained for a single candidate region.

In this case, as compared with a region specular-reflected from a mucous membrane and a food residue floating above or accumulated on a mucous membrane (for example, the candidate regions A2 to A5 as illustrated in FIG. 3), the pixel values less greatly change from those of the mucous membrane surface therearound in a region of aphthous ulcers and ulcer existing in the outermost layer of a mucous membrane (for example, the candidate region A1 as illustrated in FIG. 3). On the other hand, as compared with proximity mucous membrane surface which is a mucous membrane surface where there is no lesion and the like (which means that it is continuous), the pixel values more greatly change from those of the mucous membrane surface therearound. Therefore, in the first embodiment, the edge strengths of the border neighboring pixels are calculated as feature data for distinguishing changes of pixel values. Thereafter, the processing in the main routine is performed back again.

In step S15, the abnormal portion region distinguishing unit 140 distinguishes an abnormal portion region based on the feature data. In the first embodiment, the abnormal portion region distinguishing unit 140 distinguishes an abnormal portion region using stochastic model like the method explained in step S12. More specifically, multiple candidate regions which respectively belong to categories such as aphthous ulcers, ulcer, food residue, specular reflection, proximity mucous membrane are sampled in advance, and feature data (i.e., edge strengths for each wavelength component) based on pixel values of border neighboring pixels of each candidate region are derived. Then, based on feature vector Fn=(fn_1, fn_2, . . . , fn_j, . . . , fn_k)$^t$ composed of feature data of sampled candidate regions (fn_j: the j-th feature data of the n-th sampled candidate region, k: the number of feature data (k=3 in the present embodiment), the average vector μ, and the variance-covariance matrix Z given by the above expressions (1-1) and (1-2) are derived for each category, and are recorded to the recording unit 50.

Then, the abnormal portion region distinguishing unit 140 generate feature vector x=(x_1, x_2, . . . , x_j, . . . , x_k)$^t$ composed of feature data of a candidate region included in the image of the processing target (x_j is the j-th feature data of a candidate region), and based on the average vector μ and the variance-covariance matrix Z of each category recorded in the recording unit 50 in advance, the abnormal portion region distinguishing unit 140 calculates, for each category, the determination index P (x) for determining whether each candidate region is a region of the category is calculated in accordance with the above expression (1-3). Thereafter, the abnormal portion region distinguishing unit 140 determines that a candidate region where the determination index P (x) with respect to categories of aphthous ulcers and ulcer is more than a determination index P (x) corresponding to another category and the value of the determination index P (x) is equal to or more than a specified threshold value is an abnormal portion region.

It should be noted that the method for distinguishing an abnormal portion region based on feature data may be not only a method using the stochastic model explained above but also other generally-used methods used for pattern recognition (decision tree, proximity method, support vector machine, and the like).

Then, In the final step S16, the calculation unit 100 outputs a distinction result of the abnormal portion region in step S15. In response thereto, the control unit 10 records the distinction result of the abnormal portion region to the recording unit 50. At this occasion, the control unit 10 may display the distinction result of the abnormal portion region on the display unit 40 and the like. Thereafter, the processing of the image processing apparatus 1 is terminated.

As described above, according to the first embodiment, the candidate region of the abnormal portion is detected based on the color information of the intraluminal image, and thereafter, the feature data based on the pixel values of the border neighboring pixels of the candidate region are calculated, and the abnormal portion region is distinguished based on the feature data, and therefore, the abnormal portion and another object in the image having the same type of color information as the abnormal portion can be distinguished from each other with a high degree of accuracy. According to the first embodiment, a region where a distance from the border pixels of the candidate region is equal to or less than a specified distance is set as a border neighboring region of each candidate region, and the feature data are calculated in such a manner that the pixels in the border neighboring region are adopted as the border neighboring pixels, and therefore, even when the detection accuracy of the candidate region is insufficient, and the border of the candidate region that has been detected is different from the original border, the difference can be compensated. As a result, the abnormal portion can be distinguished with a high degree of accuracy.

Second Embodiment

Next, a second embodiment of the present invention will be explained.

Figure 11:
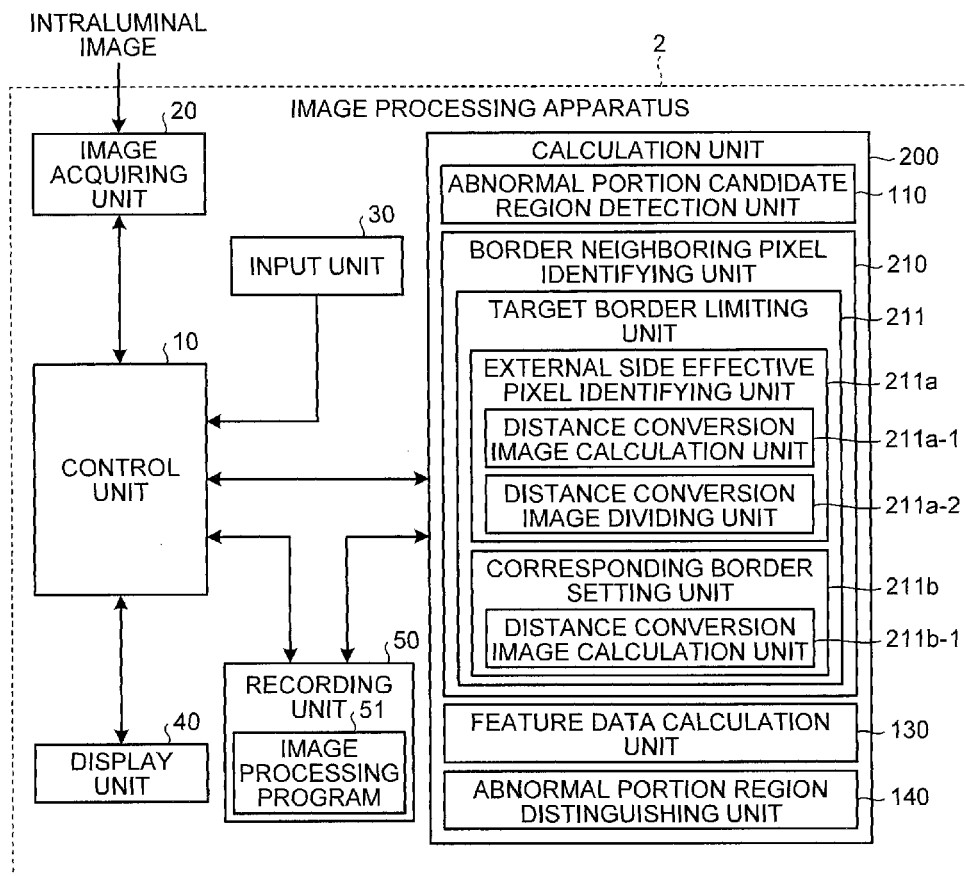
FIG. 11 is a block diagram illustrating a configuration of an image processing apparatus according to a second embodiment of the present invention.

FIG. 11 is a block diagram illustrating a configuration of an image processing apparatus according to the second embodiment. As illustrated in FIG. 11, an image processing apparatus 2 according to the second embodiment has a calculation unit 200 instead of the calculation unit 100 as illustrated in FIG. 1. It should be noted that the configuration of the image processing apparatus 2 is the same as the one illustrated in FIG. 1 except the calculation unit 200.

The calculation unit 200 includes an abnormal portion candidate region detection unit 110, a border neighboring pixel identifying unit 210, a feature data calculation unit 130, and an abnormal portion region distinguishing unit 140. Among them, the configuration and the operation of the abnormal portion candidate region detection unit 110, the feature data calculation unit 130, and the abnormal portion region distinguishing unit 140 are the same as those of the first embodiment.

The border neighboring pixel identifying unit 210 includes a target border limiting unit 211 configured to limit a border, which serves as a basis for identifying border neighboring pixels, into a part of all the periphery of the border of the candidate region, and identifies border neighboring pixels for the partial border thus limited.

More specifically, the target border limiting unit 211 includes an external side effective pixel identifying unit 211a configured to identify pixels in a region effective for calculation of feature data (which may be hereinafter referred to as effective pixel) from an external side region which is a specified range at the outside of the border pixels of the candidate region, and a corresponding border setting unit 211*b* configured to set a border corresponding to effective pixels. Among them, the external side effective pixel identifying unit 211*a* includes a distance conversion image calculation unit 211*a*-1 and a distance conversion image dividing unit 211*a*-2, and identifies pixels located at a specified distance from the border pixels in each distance conversion region as effective pixels in the candidate region corresponding to the distance conversion region.

On the other hand, the corresponding border setting unit 211*b* includes a distance conversion image calculation unit 211*b*-1 configured to calculate a distance conversion image representing a distance between an effective pixel and each pixel in an image, and sets a border within a specified distance from effective pixels as a border corresponding to the effective pixels.

Next, operation of the image processing apparatus 2 will be explained. Overall operation of the image processing apparatus 2 is the same as that of the first embodiment, but the contents of processing for identifying border neighboring pixels of a candidate region of an abnormal portion detected from an intraluminal image executed by the border neighboring pixel identifying unit 210 in step S13 of FIG. 2 are different from the first embodiment.

Figure 12:
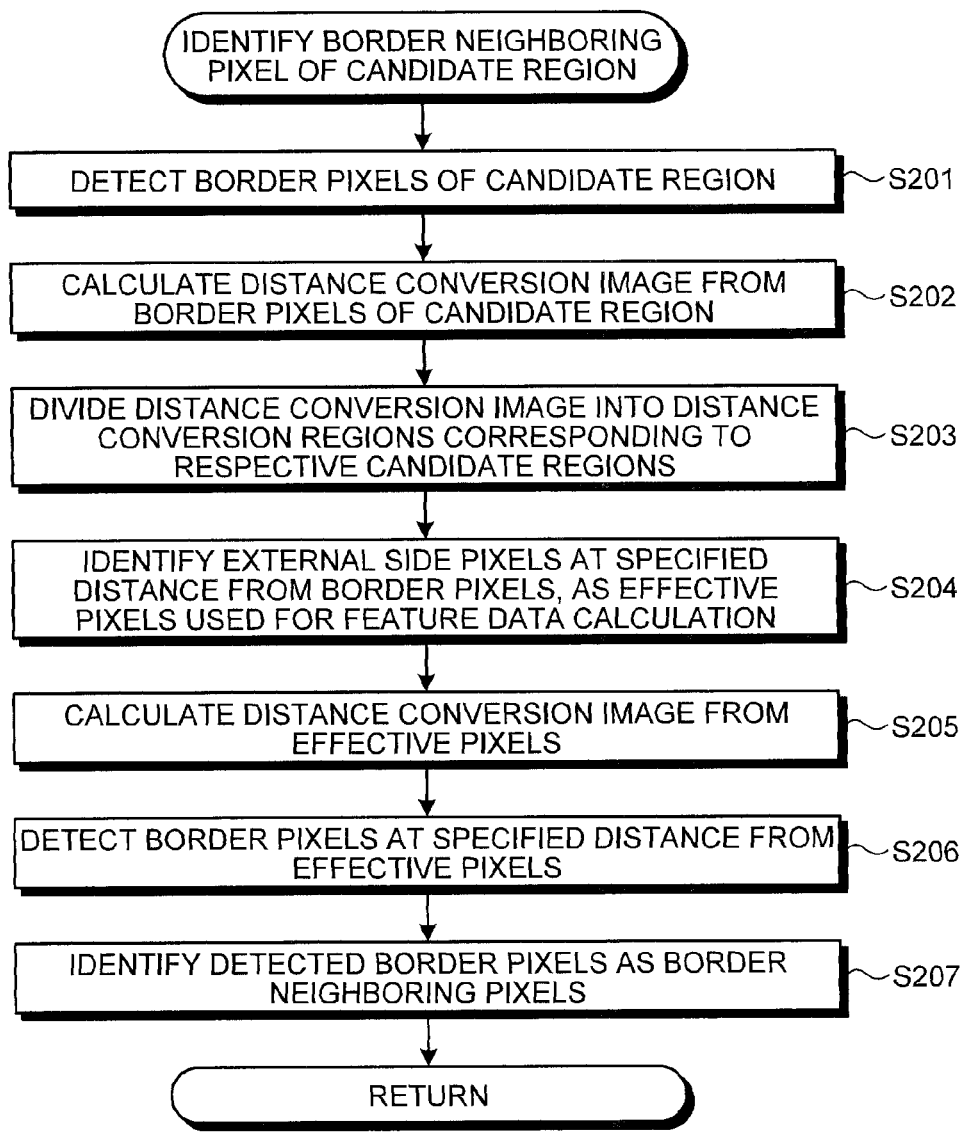
FIG. 12 is a flowchart illustrating operation of a border neighboring pixel identifying unit as illustrated in FIG. 11.
Figure 13:
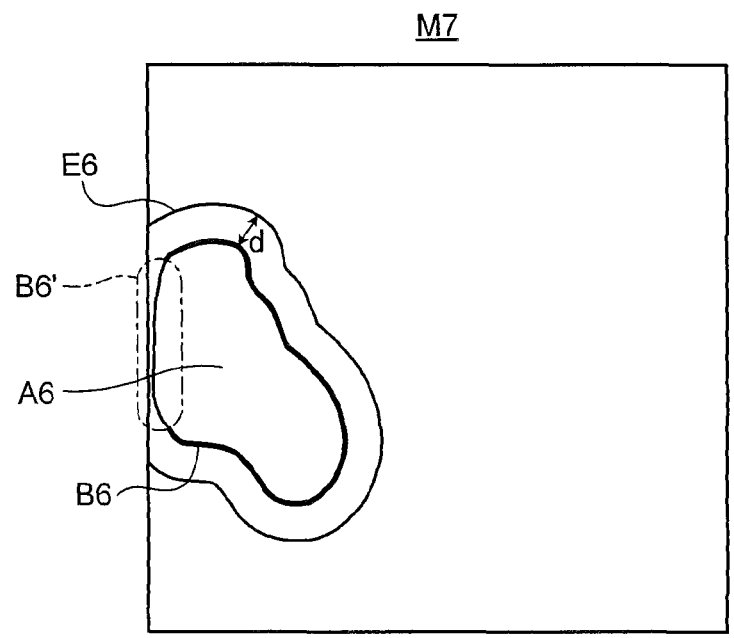
FIG. 13 is a schematic diagram for explaining an identifying method of border neighboring pixels according to the second embodiment.
Figure 14:
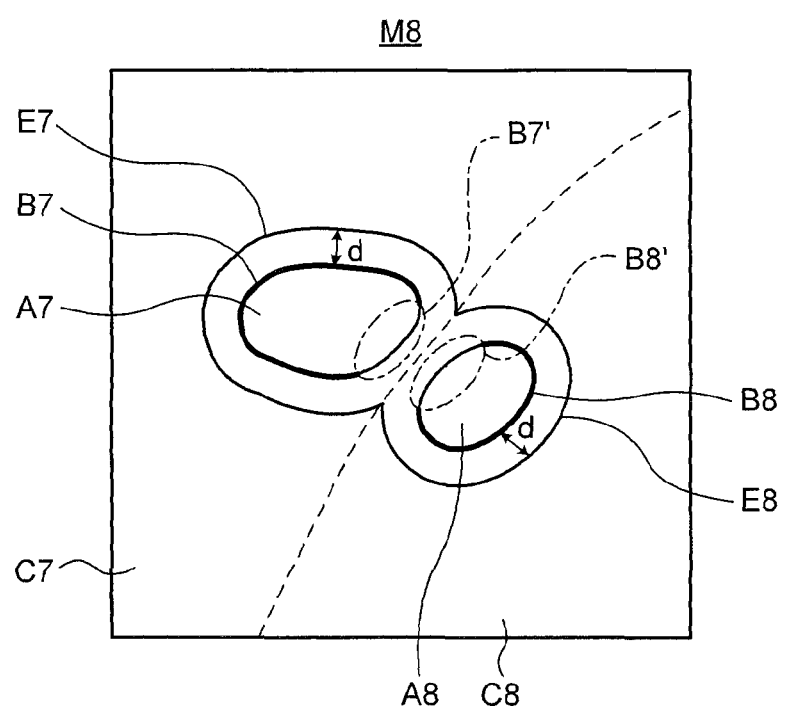
FIG. 14 is a schematic diagram for explaining an identifying method of border neighboring pixels according to the second embodiment.

FIG. 12 is a flowchart illustrating operation of the border neighboring pixel identifying unit 210 in details. FIGS. 13 and 14 are schematic diagrams for explaining identifying method of border neighboring pixels.

First, in step S201, the border neighboring pixel identifying unit 210 detects border pixels of a candidate region. The details of the processing in step S201 are the same as step S131 as illustrated in FIG. 5.

In step S202, the distance conversion image calculation unit 211*a*-1 calculates a distance conversion image representing a distance between a border pixel of candidate regions and each pixel in an image. The details of processing in step S202 are the same as step S132 as illustrated in FIG. 5.

In step S203, the distance conversion image dividing unit 211*a*-2 divides the distance conversion image into distance conversion regions corresponding to the respective candidate regions. The details of processing in step S203 are the same as step S133 as illustrated in FIG. 5.

In step S204, the external side effective pixel identifying unit 211*a* identifies external side pixels, which are pixels at a specified distance from border pixels, as effective pixels. In this case, the external side pixels are pixels away from the border pixels of the candidate region by a specified distance d toward the outside of the candidate region, in a distance conversion region corresponding to each candidate region.

At this occasion, for example, when the candidate region A6 is in contact with the end portion of the image M7 as shown in the image M7 of FIG. 13, effective pixels are not identified for the pixel group B6' in proximity to the end portion of the image M7 in the border pixel group B6. In a case where, for example, the candidate regions A7, A8 included in the distance conversion regions C7, C8, respectively, are proximity to each other with an interval which is twice the specified distance d or less as shown by the image M8 of FIG. 14, effective pixels are not identified for the border pixel groups B7', B8' which are in proximity to each other with a distance which is twice the distance d or less in the border pixel groups B7, B8.

In step S205, the distance conversion image calculation unit 211*b*-1 calculates a distance conversion image representing a distance of each pixel in the image from an effective pixel. The calculation method of the distance conversion image is the same as step S132 as illustrated in FIG. 5.

In step S206, the corresponding border setting unit 211*b* detects border pixels at a specified distance from effective pixels.

In step S207, the border neighboring pixel identifying unit 210 identifies the border pixels detected in step S206 as border neighboring pixels. Therefore, in the border pixels, the pixels in a portion adjacent to an end portion of the image and the pixels in a portion of candidate regions in proximity to each other within a specified distance are not identified as border neighboring regions. Thereafter, the processing in the main routine is performed back again.

As a more specific example, in the case of the image M7 as illustrated in FIG. 13, the border pixel group B6 (the portion of the thick line) at the specified distance d from the effective pixel group E6 is detected in step S206, based on the distance conversion image representing the distances from the effective pixel group E6 calculated in step S205. Only the border pixel group B6 is identified as the border neighboring pixels in step S207.

In the case of the image M8 as illustrated in FIG. 14, the border pixel groups B7, B8 (the portion of the thick line) at the specified distance d from the effective pixel groups E7, E8 are detected in step S206, based on the distance conversion image representing the distances from the effective pixel groups E7, E8 calculated in step S205. Only the border pixel groups B7, B8 are identified as the border neighboring pixels in step S207.

As explained above, according to the second embodiment, the external side pixels located at a specified distance from border pixels are identified as pixels in a region effective for calculation of feature data, and feature data are calculated based on a border corresponding to the pixels in the effective region, and therefore, the change of the pixel values in a portion of a candidate region in contact with an edge of the image and the change of the pixel values between candidate regions in proximity to each other are excluded, and the feature data can be calculated based on the change of the pixel values from those of the mucous membrane surface therearound. As a result, the abnormal portion can be distinguished with a high degree of accuracy.

Modification

Next, a modification of the second embodiment will be explained.

Figure 15:
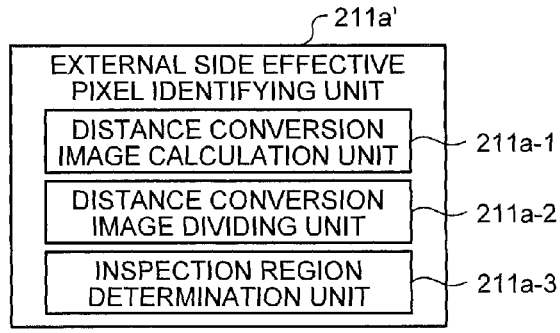
FIG. 15 is a block diagram illustrating a configuration of an external side effective pixel identifying unit according to a modification of the second embodiment.

The image processing apparatus according to the modification of the second embodiment includes an external side effective pixel identifying unit 211*a*' as illustrated in FIG. 15 instead of an external side effective pixel identifying unit 211*a* as illustrated in FIG. 11. The configuration of the image processing apparatus is the same as the one illustrated in FIG. 11 except the external side effective pixel identifying unit 211*a*'.

The external side effective pixel identifying unit 211*a*' includes not only the distance conversion image calculation unit 211*a*-1 and the distance conversion image dividing unit 211*a*-2, which are the same as those of the second embodiment, but also an inspection region determination unit 211*a*-3 configured to determine whether pixels in an external side region are included in a target region where an abnormal portion is detected (which may be hereinafter referred to as inspection target region), and identifies, as effective pixels, pixels in the external side region determined to be included in the inspection target region.

Figure 16:
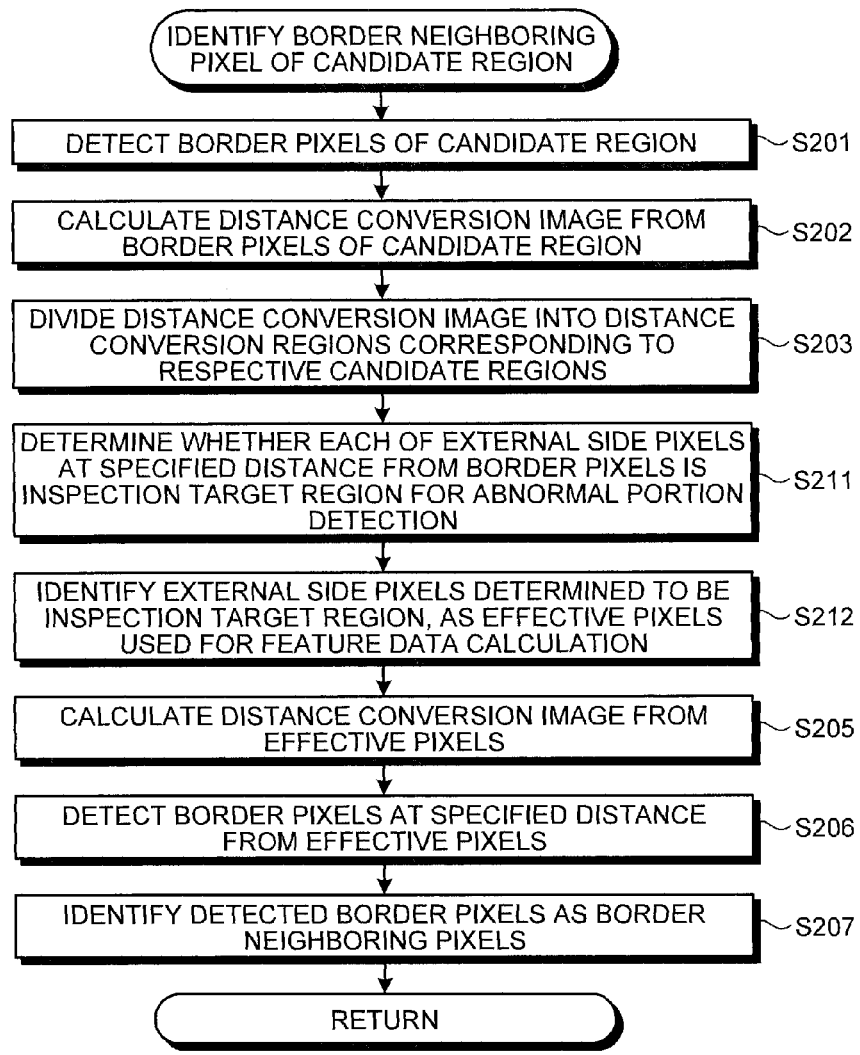
FIG. 16 is a flowchart illustrating operation of a border neighboring pixel identifying unit according to a modification of the second embodiment.
Figure 17:
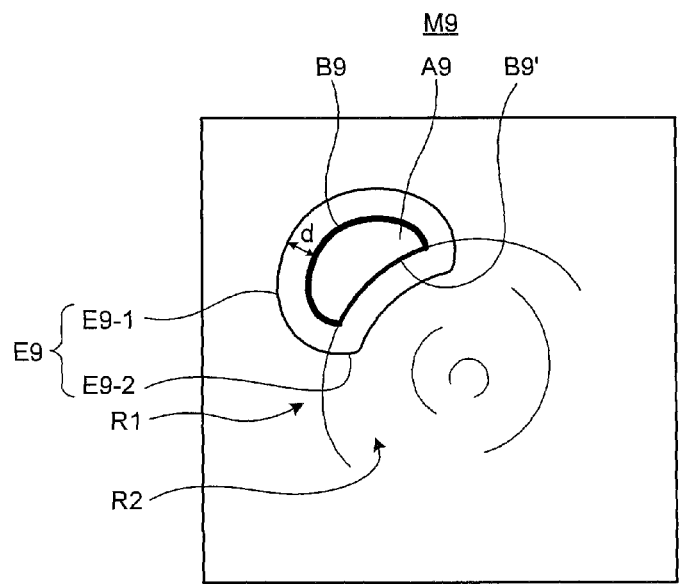
FIG. 17 is a schematic diagram for explaining a determination method of an inspection target region according to a modification of the second embodiment.

Next, operation of the image processing apparatus according to the present modification will be explained. FIG. 16 is a flowchart illustrating operation of the border neighboring pixel identifying unit according to the present modification. FIG. 17 is a schematic diagram for explaining the determination method of the inspection target region. Operation of steps S201 to S203 illustrated in FIG. 16 is the same as the second embodiment.

In step S211 subsequent to step S203, the inspection region determination unit 211a-3 determines whether each of the external side pixels located at a specified distance from border pixels is included in an inspection target region for abnormal portion detection. In this case, in a case where there is a region (non-inspection target region) other than a mucous membrane region which is the inspection target region such as colored residual and a deep portion (dark portion) of a lumen at a periphery at the outside of a candidate region (external side), it is not appropriate to calculate feature data based on pixels in proximity to a border between this non-inspection target region and the candidate region. This is because, at the border between the non-inspection target region and the candidate region, the pixel values greatly change, and therefore, the average values of the feature data used for the abnormal portion determination are greatly affected by the change of the pixel values at the border.

Therefore, the inspection region determination unit 211a-3 detects whether the external side pixels are the mucous membrane region which is the inspection target region. More specifically, like step S12, the inspection region determination unit 211a-3 identifies a region indicating the color of the mucous membrane region based on the color information of each pixel in the image, and determines that the external side pixels included in the region are the mucous membrane region (inspection target region).

For example, in a case where a candidate region A9 is detected at an end portion of a fold region R1 of a mucous membrane as shown in an image M9 of FIG. 17, an external side pixel group E9-1 at the fold region R1 of the external side pixel group E9 located at the specified distance d from a border pixel group B9 of the candidate region A9 is determined to be the inspection target region, and an external side pixel group E9-2 at a deep portion region R2 of the lumen of the external side pixel group E9 located at the specified distance d from the border pixel group B9 of the candidate region A9 is determined to be outside of the inspection target region.

In step S212, the external side effective pixel identifying unit 211a' identifies the external side pixels determined to be included in the inspection target region as pixels in a region effective for calculation of the feature data (effective pixels). For example, in the case of FIG. 17, the external side pixel group E9-1 is identified as the effective pixels.

The subsequent steps S205 to S207 are the same as those of the second embodiment. For example, in the case of the image M9 as illustrated in FIG. 17, the border pixel group B9 at the specified distance d from the external side pixel group E9-1 (the portion of the thick line) is detected in step S206 based on the distance conversion image representing distances form the external side pixel (effective pixel) group E9-1 calculated in step S205. Only the border pixel group B9 is identified as the border neighboring pixels in step S207. More specifically, border pixel group B9' at a side adjacent to the non-inspection region (the deep portion region R2 of the lumen) is not identified as border neighboring pixels.

As explained above, according to the modification of the second embodiment, the external side pixels determined to be included in the inspection target region are identified as pixels in a region effective for calculation of the feature data, and the feature data are calculated based on the pixel values of the border pixels corresponding to the pixels of the effective region, and therefore, the change of the pixel values at the border adjacent to the non-inspection target region in the border pixels of the candidate region is excluded, and the feature data can be calculated based on the change of the pixel values from the mucous membrane surface therearound. As a result, the abnormal portion can be distinguished with a high degree of accuracy.

Third Embodiment

Next, a third embodiment of the present invention will be explained.

Figure 18:
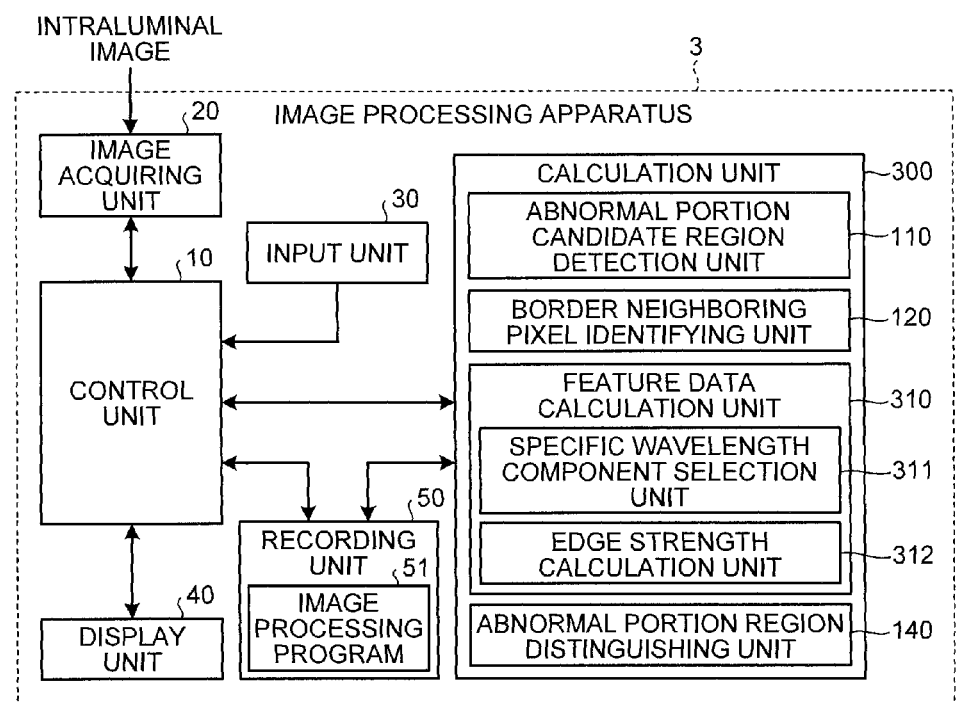
FIG. 18 is a block diagram illustrating a configuration of an image processing apparatus according to a third embodiment of the present invention.

FIG. 18 is a block diagram illustrating a configuration of an image processing apparatus according to the third embodiment. As illustrated in FIG. 18, the image processing apparatus 3 according to the third embodiment has a calculation unit 300 instead of the calculation unit 100 as illustrated in FIG. 1. The configuration of the image processing apparatus 3 is the same as the one as illustrated in FIG. 1 other than the calculation unit 300.

The calculation unit 300 includes an abnormal portion candidate region detection unit 110, a border neighboring pixel identifying unit 120, a feature data calculation unit 310, and an abnormal portion region distinguishing unit 140. Among them, the configuration and the operation of the abnormal portion candidate region detection unit 110, the border neighboring pixel identifying unit 120, and the abnormal portion region distinguishing unit 140 are the same as those of the first embodiment.

The feature data calculation unit 310 includes a specific wavelength component selection unit 311 configured to select a specific wavelength component identified in accordance with the degree of absorption in a living body, and an edge strength calculation unit 312 configured to calculate the edge strength of the specific wavelength component selected from among the pixel values of the border neighboring pixels.

Next, operation of the image processing apparatus 3 will be explained. Overall operation of the image processing apparatus 3 is the same as the first embodiment, but the contents of processing for calculating feature data of pixel values of the border neighboring region executed by the feature data calculation unit 310 in step S14 of FIG. 2 are different from the first embodiment.

Figure 19:
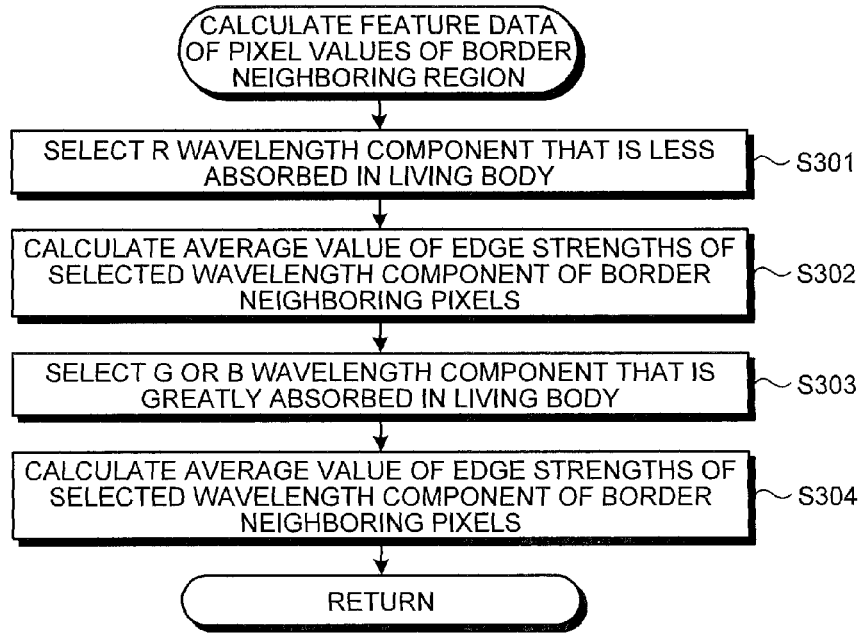
FIG. 19 is a flowchart illustrating operation of a feature data calculation unit as illustrated in FIG. 18.

FIG. 19 is a flowchart illustrating operation of the feature data calculation unit 310 in detail. First, in step S301, the specific wavelength component selection unit 311 selects R wavelength component that is less absorbed in the living body. In this case, an image-capturing distance of aphthous ulcers and ulcer existing in the outermost layer of the mucous membrane is about the same as the image-capturing distance of the mucous membrane surface therearound. In contrast, the image-capturing distance of food residue floating above or accumulated on the mucous membrane is shorter (which is closer) than the image-capturing distance of the mucous membrane surface therearound. The difference of such image-capturing distance can be easily confirmed by the R wavelength component that is less absorbed in the living body. Therefore, in step S301, the R wavelength component is selected as the specific wavelength component.

In step S302, the edge strength calculation unit 312 calculates the average value of the edge strengths of the specific wavelength component selected in step S301 with regard to the border neighboring pixels. The details of this processing are the same as steps S141 and S142 illustrated in FIG. 10 except that the calculation target of the average values of the edge strengths is only the specific wavelength component.

In step S303, the specific wavelength component selection unit 311 selects G wavelength component or B wavelength component which is greatly absorbed in the living body. In this case, aphthous ulcers and ulcer that occur together with the change of a living tissue have a color tone different from the mucous membrane surface therearound regardless of the image-capturing distance. In contrast, the mucous membrane surface of which image is captured by a medical observation apparatus such as a capsule endoscope in proximity (close-up mucous membrane region) has a color tone different from the mucous membrane surface therearound, since the image-capturing distance is short and the R wavelength component is saturated. Such difference in the color tones according to the image-capturing distance can be easily confirmed by G wavelength component or B wavelength component which is greatly absorbed in the living body. Therefore, in step S303, G wavelength component or B wavelength component is selected as the specific wavelength component.

In step S304, the edge strength calculation unit 312 calculates the average value of the edge strengths of the specific wavelength component selected in step S303 with regard to the border neighboring pixels. The details of this processing are the same as steps S141 and S142 illustrated in FIG. 10 except that the calculation target of the average value of the edge strengths is only the specific wavelength component.

Thereafter, the processing in the main routine is performed back again. At this occasion, in step S15 of FIG. 2, the average value of the edge strengths calculated in step S302 and the average value of the edge strengths calculated in step S304 are used separately to distinguish the abnormal portion region. Therefore, the food residue region and the abnormal portion region are distinguished from each other from the average value of the edge strengths based on the R wavelength component. The close-up mucous membrane region and the abnormal portion region are distinguished from each other from the average value of the edge strengths based on G wavelength component or B wavelength component. It should be noted that, as necessary, they may be distinguished from each other using only any one of the average values.

As explained above, according to the third embodiment, in accordance with the degree of absorption in the living body, the specific wavelength component which is used for identification is selected, and the feature data are calculated, and therefore, the feature data suitable for distinguishing the abnormal portion and the food residue or the abnormal portion and the proximity mucous membrane can be calculated. As a result, the abnormal portion can be distinguished with a high degree of accuracy.

It should be noted that the feature data calculation unit 310 explained above may be applied instead of the feature data calculation unit 130 as illustrated in FIG. 11.

Fourth Embodiment

Next, a fourth embodiment of the present invention will be explained.

Figure 20:
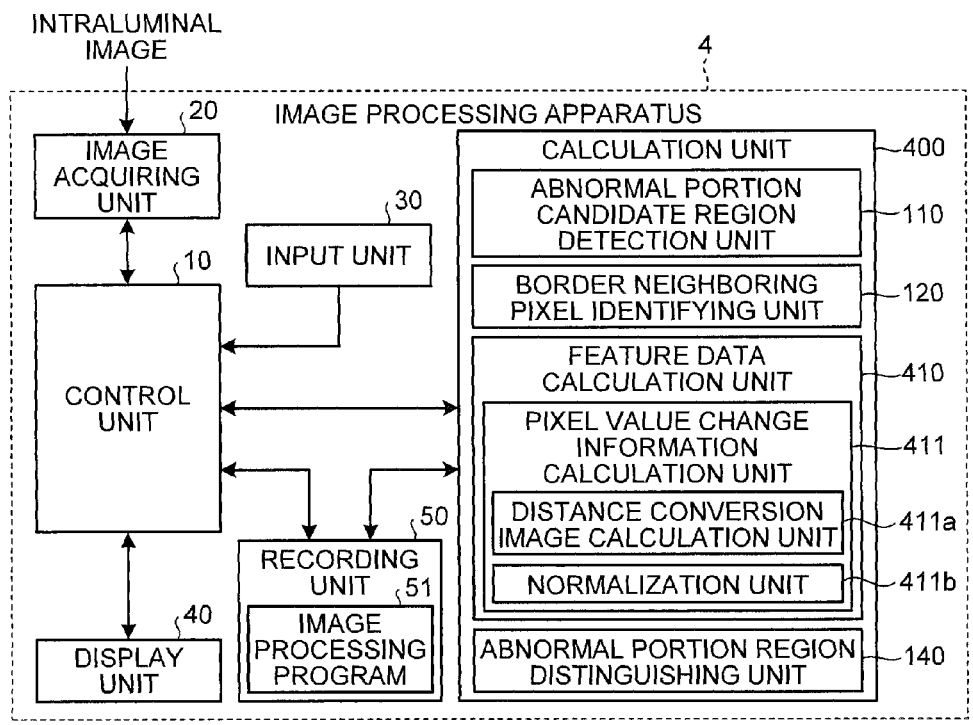
FIG. 20 is a block diagram illustrating a configuration of an image processing apparatus according to a fourth embodiment of the present invention.

FIG. 20 is a block diagram illustrating a configuration of an image processing apparatus according to the fourth embodiment. As illustrated in FIG. 20, the image processing apparatus 4 according to the fourth embodiment has a calculation unit 400 instead of the calculation unit 100 as illustrated in FIG. 1. It should be noted that the image processing apparatus 4 is the same as the one illustrated in FIG. 1 except the calculation unit 400.

The calculation unit 400 includes an abnormal portion candidate region detection unit 110, a border neighboring pixel identifying unit 120, a feature data calculation unit 410, and an abnormal portion region distinguishing unit 140. Among them, the configuration and the operation of the abnormal portion candidate region detection unit 110, the border neighboring pixel identifying unit 120, and the abnormal portion region distinguishing unit 140 are the same as those of the first embodiment.

The feature data calculation unit 410 has a pixel value change information calculation unit 411 configured to calculate pixel value change information representing the change of pixel values between the inside and the outside of the border pixels of the candidate region, and adopts the pixel value change information as feature data. More specifically, the pixel value change information calculation unit 411 includes a distance conversion image calculation unit 411a configured to calculate a distance conversion image representing a distance between a border pixel and each pixel in an image, and a normalization unit 411b configured to normalize pixel value change information so that the pixel values of the border pixels become the same values.

Next, operation of the image processing apparatus 4 will be explained. Overall operation of the image processing apparatus 4 is the same as the first embodiment, but the contents of processing for calculating feature data of pixel values of the border neighboring region executed by the feature data calculation unit 410 in step S14 of FIG. 2 are different from the first embodiment.

Figure 21:
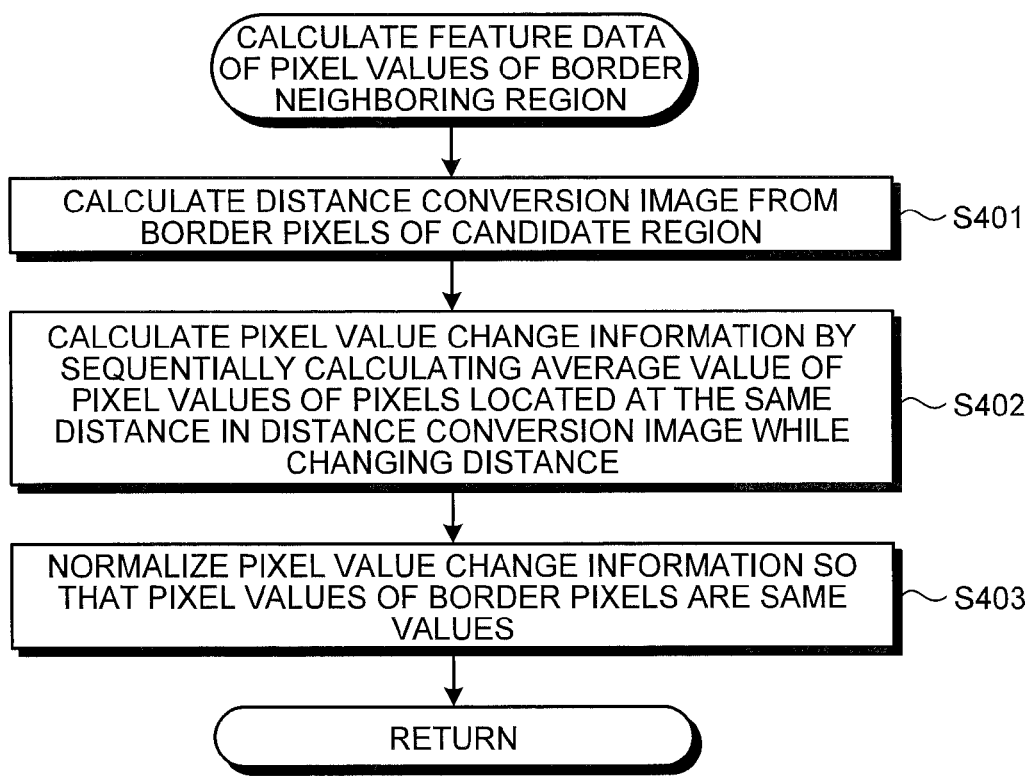
FIG. 21 is a flowchart illustrating operation of a feature data calculation unit as illustrated in FIG. 20.
Figure 22:
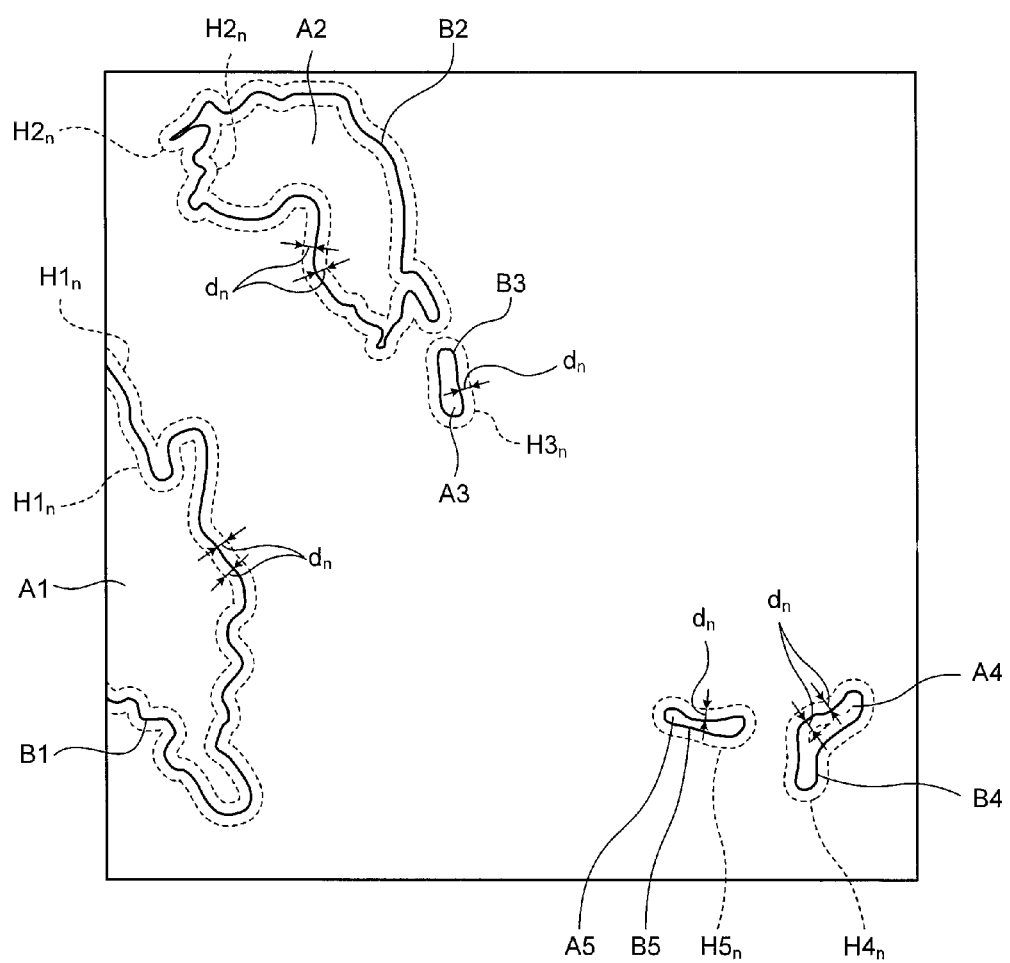
FIG. 22 is a schematic diagram for explaining a calculation method of pixel value change information.

FIG. 21 is a flowchart illustrating operation of the feature data calculation unit 410 in details. FIG. 22 is a schematic diagram for explaining a calculation method of pixel value change information.

First, in step S401, the distance conversion image calculation unit 411a calculates a distance conversion image representing a distance between a border pixel and each pixel in an image. The details of the processing in step S401 are the same as step S132 as illustrated in FIG. 5.

In step S402, for each distance conversion region, the pixel value change information calculation unit 411 calculates pixel value change information by sequentially calculating the average value of the pixel values of a pixel group which is at the same distance in the distance conversion image (i.e., pixel group where the distances from the border of the candidate region are the same) while changing the distance.

For example, in the case of the image M10 as illustrated in FIG. 22, the average value of the pixel values is calculated for each of the pixel groups $H1_n$ to $H5_n$ spaced apart from the border pixel groups B1 to B5 by the distance $d_n$. In this case, $n=0, \pm1, \pm2, \ldots$, and when $n=0$, $d_n=0$ holds. When n increases, the distance $d_n$ increases to the outside of the border pixel groups B1 to B5, and when n decreases, the distance $d_n$ increases to the inside of the border pixel groups B1 to B5.

Figure 23:
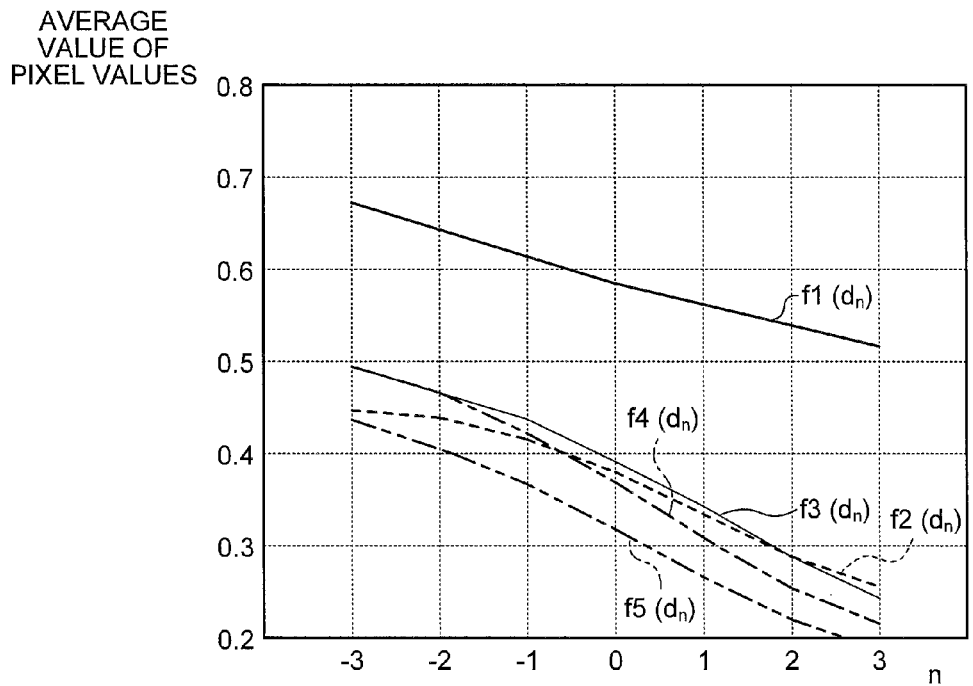
FIG. 23 is a graph illustrating an average value of pixel values corresponding to a pixel group as illustrated in FIG. 22.

FIG. 23 is a graph illustrating average values $f1(d_n)$ to $f5(d_n)$ of pixel values corresponding to the pixel groups $H1_n$ to $H5_n$, respectively. In this case, the average values $f1(d_n)$ to $f5(d_n)$ are such that when the graph is located at a higher side, the overall brightness of the corresponding candidate region is higher, and accordingly, the image-capturing distance can be determined to be shorter. In the case of the image M10 As illustrated in FIG. 22, the image-capturing distance of the candidate region A1 of which average value f1 ($d_n$) is significantly high is short (existing at the closer side with respect to the screen), and the image-capturing distances of the other candidate regions A2 to A5 are relatively long (existing at the deeper side with respect to the screen).

In step S403, the normalization unit 411b normalizes the pixel value change information so that the average values of the pixel values of the border pixels become the same value. Accordingly, the size of the average value due to the difference of the image-capturing distances explained above is corrected.

Figure 24:
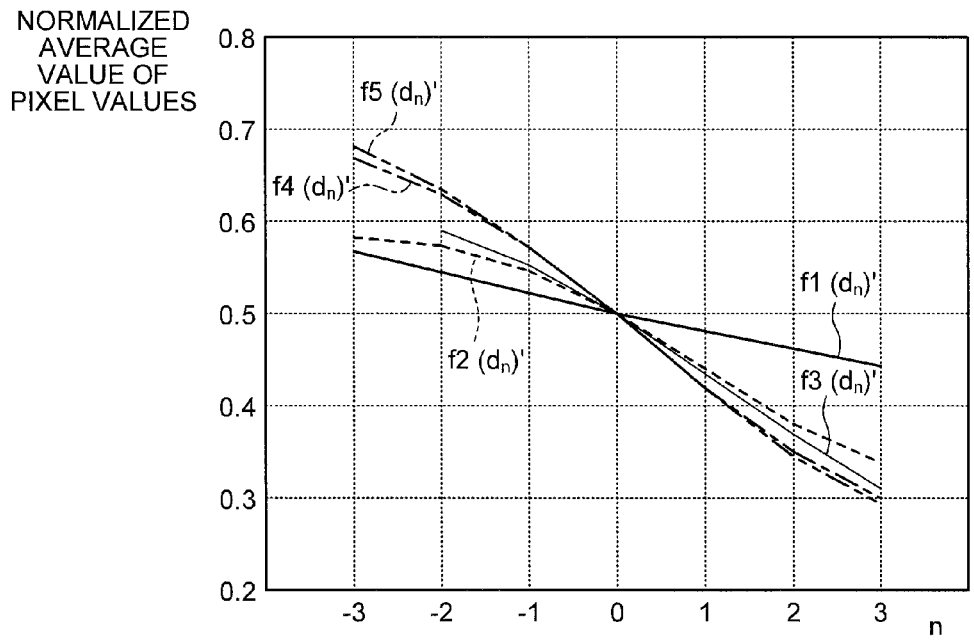
FIG. 24 is a graph illustrating a normalized average value of pixel values.

FIG. 24 is a graph obtained by normalizing the average values f1 ($d_n$) to f5 ($d_n$) of the pixel values as illustrated in FIG. 23. As illustrated in FIG. 24, the changes (inclinations) of the normalized average values f1 ($d_n$)' to f5 ($d_n$)' indicate the changes of the pixel values in proximity to the border pixel groups B1 to B5 corresponding to the candidate regions A1 to A5, respectively. For example, in FIG. 24, the change of the average value f1 ($d_n$)' is the least, and the changes of the average values f4 ($d_n$)', f5 ($d_n$)' are relatively large. The pixel value change information calculation unit 411 outputs the thus calculated average values f1 ($d_n$)' to f5 ($d_n$)' as the pixel value change information (pixel value profiles).

Thereafter, the processing in the main routine is performed back again. In step S15 as illustrated in FIG. 2, the abnormal portion region distinguishing unit 140 distinguishes the abnormal portion region based on the pixel value change information calculated in step S14. More specifically, the value corresponding to each distance $d_n$ in the pixel value change information is adopted as feature data, and like the first embodiment, the determination index P (x) is calculated, and the determination index P (x) is subjected to threshold value processing, so that the abnormal portion region is distinguished. For example, in the case of the image M10 as illustrated in FIG. 22, the candidate region A1 of which average value f1 ($d_n$) changes less greatly is determined to be an abnormal portion region.

As described above, according to the fourth embodiment, pixel value change information obtained by sequentially calculating the average value of the pixel values of the pixels where the distance from the border pixels are the same in the border neighboring pixels while changing the distance is adopted as feature data, and therefore, the feature data that are less likely to be affected by noises and that indicate the change of the detailed pixel values between the candidate region and the mucous membrane surface around the candidate region and can be calculated. According to the fourth embodiment, the pixel value change information is normalized so that the pixel values of the border pixels are of the same value, and therefore, the feature data for which the differences of the magnitudes of the pixel values are corrected in accordance with the image-capturing distances can be calculated. Therefore, the abnormal portion can be detected with a high degree of accuracy.

It should be noted that the feature data calculation unit 410 explained above may be applied instead of the feature data calculation unit 130 as illustrated in FIG. 11.

Fifth Embodiment

Next, a fifth embodiment of the present invention will be explained.

Figure 25:
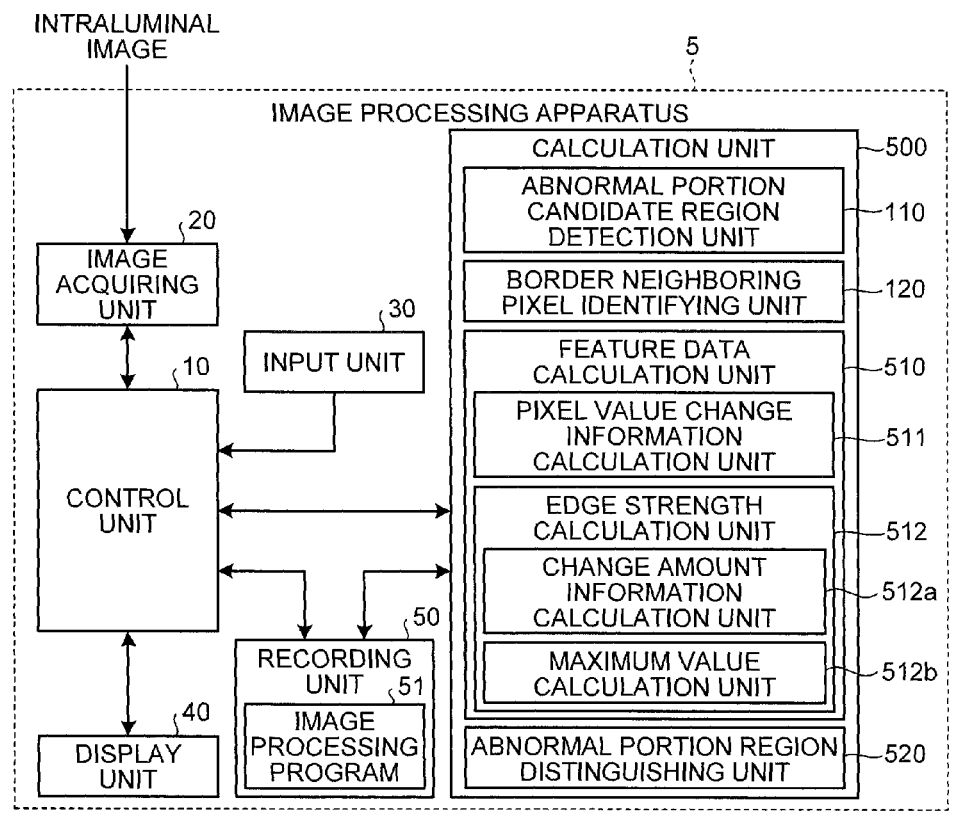
FIG. 25 is a block diagram illustrating a configuration of an image processing apparatus according to a fifth embodiment of the present invention.

FIG. 25 is a block diagram illustrating a configuration of an image processing apparatus according to the fifth embodiment. As illustrated in FIG. 25, the image processing apparatus 5 according to the fifth embodiment has a calculation unit 500 instead of the calculation unit 100 as illustrated in FIG. 1. The configuration of the image processing apparatus 5 is the same as the one illustrated in FIG. 1 except the calculation unit 500.

The calculation unit 500 includes an abnormal portion candidate region detection unit 110, a border neighboring pixel identifying unit 120, a feature data calculation unit 510, and an abnormal portion region distinguishing unit 520. The feature data calculation unit 510 includes a pixel value change information calculation unit 511 configured to calculate pixel value change information representing the change of the pixel values between the inside and the outside of the border pixels of the candidate region, and an edge strength calculation unit 512. Among them, the edge strength calculation unit 512 includes a change amount information calculation unit 512a configured to calculate the change amount information representing the change amounts of the pixel values based on the pixel value change information, and a maximum value calculation unit 512b configured to calculate the maximum value of the change amounts. The abnormal portion region distinguishing unit 520 distinguishes an abnormal portion region based on the maximum value calculated by the feature data calculation unit 510 as feature data. The configuration and the operation of the abnormal portion candidate region detection unit 110 and the border neighboring pixel identifying unit 120 are the same as the first embodiment.

Next, operation of the image processing apparatus 5 will be explained. Overall operation of the image processing apparatus 5 is the same as the first embodiment, but the contents of processing for calculating feature data of pixel values of the border neighboring region executed by the feature data calculation unit 510 in step S14 of FIG. 2 are different from the first embodiment.

Figure 26:
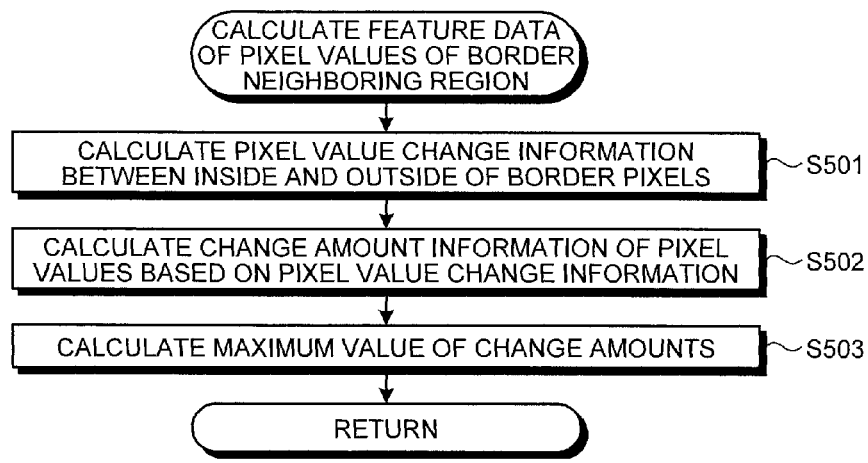
FIG. 26 is a flowchart illustrating operation of a feature data calculation unit as illustrated in FIG. 25.

FIG. 26 is a flowchart illustrating operation of the feature data calculation unit 510. First, in step S501, the pixel value change information calculation unit 511 calculates the pixel value change information between the inside and the outside of the border pixel (see FIG. 24). The details of processing in step S501 is the same as steps S401 to S403 as illustrated in FIG. 21.

Figure 27:
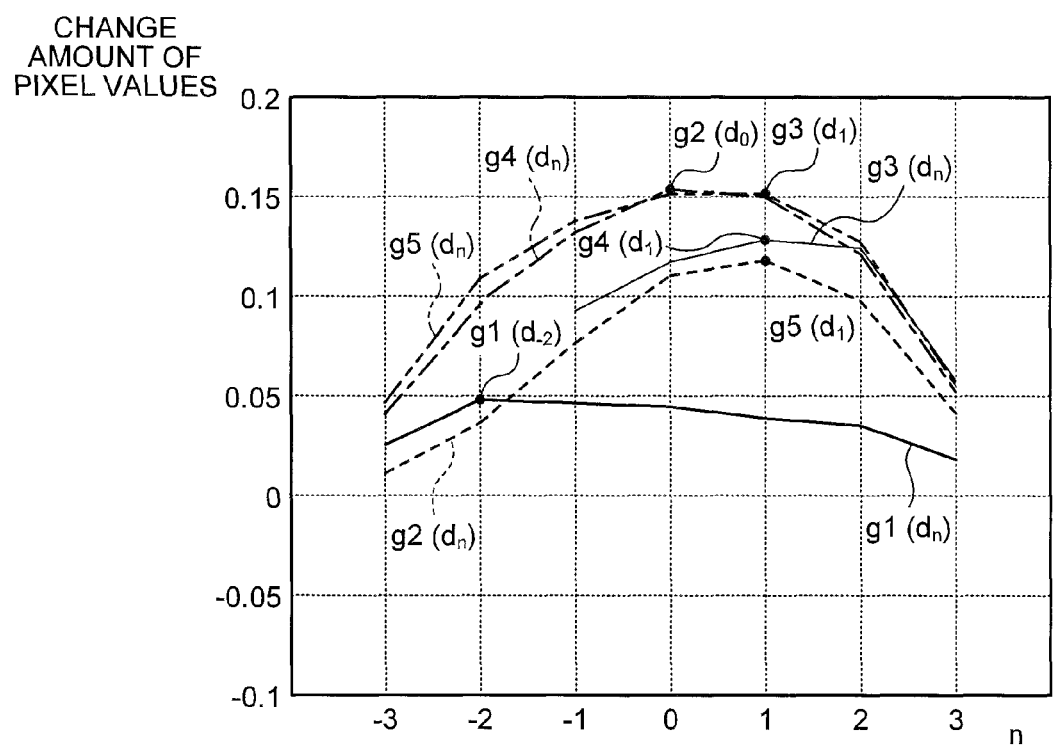
FIG. 27 is a graph illustrating change amount information of a pixel value (derivative value).

In step S502, the change amount information calculation unit 512a calculates the change amount information of the pixel values based on the pixel value change information. More specifically, the change amount information calculation unit 512a calculates the derivative value of the average value of the pixel values calculated in step S501. FIG. 27 is a graph illustrating derivative values g1 ($d_n$) to g5 ($d_n$) corresponding to the average values f1 ($d_n$)' to f5 ($d_n$)', respectively, as illustrated in FIG. 24.

Further, in step S503, the maximum value calculation unit 512b calculates the maximum value of the change amounts based on the change amount information corresponding to each candidate regions A1 to A5. For example, in the case of FIG. 27, the maximum values g1 ($d_{-2}$) g2 ($d_0$) g3 ($d_1$), g4 ($d_1$), g5 ($d_1$) are calculated from the derivative values g1 ($d_n$) to g5 ($d_n$), respectively.

The feature data calculation unit 510 outputs the thus calculated maximum value to the feature data.

Thereafter, the processing in the main routine is performed back again. In step S15 as illustrated in FIG. 2, the abnormal portion region distinguishing unit 520 applies threshold value processing on the feature data calculated in step S14 (the maximum value of the change amounts), thus distinguishing the abnormal portion region. For example, in the case of the image M10 as illustrated in FIG. 22, the candidate region A1 of which maximum value g1 (d$_{-2}$) is small is determined to be the abnormal portion region.

As described above, according to the fifth embodiment, the change amount information of the pixel values is calculated based on the pixel value change information between the inside of the outside of the border pixel, and therefore, the feature data indicating the change amounts of the detailed pixel values between the candidate region and the mucous membrane surface around the candidate region can be calculated. According to the fifth embodiment, the maximum value of the change amounts is calculated, and even when the degree of accuracy of the detection of the candidate region is insufficient, and there is difference between the border of the detected candidate region and the original border, the difference thereof can be compensated. As a result, the abnormal portion can be distinguished with a high degree of accuracy.

The image processing apparatus according to the first to fifth embodiments and the modification thereof explained above can be achieved by causing an image processing program recorded in a recording apparatus to be executed by a computer system such as a personal computer and a work station. Such computer system may be used and connected to devices such as other computer systems and servers via a local area network, a wide area network (LAN/WAN), and a public circuit such as the Internet. In this case, the image processing apparatus according to the first to fifth embodiments and the modification thereof may obtain image data of an intraluminal image via these networks, may output an image processing result to various kinds of output devices (a viewer, a printer, and the like) connected via these networks, and may store an image processing result to a storage apparatus connected via these networks (a recording apparatus, a reading apparatus therefor, and the like).

It should be noted that the present invention is not limited to the first to fifth embodiments and the modification thereof, and various kinds of inventions can be made by combining, as necessary, multiple constituent elements disclosed in each embodiment and modification. For example, an invention can be made by removing some of the constituent elements from all the constituent elements indicated in each embodiment and modification, or an invention can be made by combining, as necessary, constituent elements shown in different embodiments and modifications.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a processor comprising hardware, wherein the processor is configured to:
   detect a plurality of candidate regions of abnormal portions based on color information of each pixel constituting an image obtained by capturing an image of an inside of a lumen of a subject;
   identify a border neighboring pixel which is a pixel existing in proximity to a border of each of the plurality of candidate regions;
   calculate feature data based on a pixel value of the border neighboring pixel; and
   distinguish an abnormal portion region based on the feature data,
   wherein the processor, in identifying the border neighboring pixel, is configured to limit a border used for identifying the border neighboring pixel, to a part of an entire periphery of the border, and
   wherein the processor, in limiting the border, is configured to:
   identify, for each of the plurality of candidate regions, an effective pixel which is a pixel in a region effective for calculation of the feature data, from an external side region which is in a specified range outwardly from a border pixel located at the border of each of the plurality of candidate regions; and
   set a border corresponding to the effective pixel.

2. The image processing apparatus according to claim 1, wherein the processor, in identifying the effective pixel, is configured to:
   calculate a distance conversion image representing a distance of each pixel in the image from the border pixel; and
   divide the distance conversion image into distance conversion regions corresponding to the candidate region,
   wherein the processor is configured to identify a pixel located at a specified distance in the distance conversion regions, as the effective pixel in the candidate region corresponding to the distance conversion regions.

3. The image processing apparatus according to claim 1, wherein the processor, in identifying the effective pixel, is configured to:
   determine whether a pixel in the external side region is included in a target region where the abnormal portion is detected; and
   identify, as the effective pixel, the pixel in the external side region determined to be included in the target region.

4. The image processing apparatus according to claim 1, wherein the processor, in setting the border corresponding to the effective pixel, is configured to:
   calculate a distance conversion image representing a distance of each pixel in the image from the effective pixel; and
   set a border which is within a specified distance from the effective pixel, as the border corresponding to the effective pixel.

5. The image processing apparatus according to claim 1, wherein the processor, in calculating the feature data, is configured to:
   select a specific wavelength component that is identified in accordance with a degree of absorption in a living body; and
   calculate the feature data based on a pixel value of the specific wavelength component of the border neighboring pixel.

6. The image processing apparatus according to claim 5, wherein the processor, in selecting the specific wavelength component, is configured to select a wavelength component that is less absorbed in the living body, as the specific wavelength component, and
wherein the processor is configured to distinguish a food residue region from the abnormal portion region in the image, in accordance with the feature data based on the pixel value corresponding to the specific wavelength component.

7. The image processing apparatus according to claim 5, wherein the processor, in selecting the specific wavelength component, is configured to select a wavelength component that is greatly absorbed in the living body, as the specific wavelength component, and
wherein the processor is configured to distinguish a close-up mucous membrane region obtained by capturing a close-up image of a mucous membrane from the abnormal portion region in the image, in accordance with the feature data based on the pixel value of the specific wavelength component.

8. The image processing apparatus according to claim 5, wherein the processor is configured to select multiple specific wavelength components different from each other.

9. The image processing apparatus according to claim 1, wherein the processor, in calculating the feature data, is configured to:
  calculate pixel value change information representing a change of pixel values between inside and outside of border pixels located at a border of the candidate region; and
  adopt the pixel value change information as the feature data.

10. The image processing apparatus according to claim 9, wherein the processor, in calculating the pixel value change information, is configured to:
  calculate a distance conversion image representing a distance of each pixel in the image from the border pixel; and
  calculate the pixel value change information by sequentially calculating an average value of pixel values of pixels located at a same distance in the distance conversion image, while changing the distance.

11. The image processing apparatus according to claim 9, wherein the processor, in calculating the pixel value change information, is configured to normalize the pixel value change information in such a way that pixel values of the border pixels are identical.

12. The image processing apparatus according to claim 1, wherein the processor, in calculating the feature data, is configured to:
  calculate an edge strength of the border neighboring pixel; and
  adopt the edge strength as the feature data.

13. The image processing apparatus according to claim 12, wherein the processor, in calculating the edge strength, is configured to:
  calculate pixel value change information representing a change of pixel values between inside and outside of border pixels located at a border of the candidate region;
  calculate change amount information representing a change amount of a pixel value based on the pixel value change information;
  calculate a maximum value of the change amount; and
  adopt the maximum value as the edge strength.

14. An image processing method comprising:
  detecting a plurality of candidate regions of abnormal portions based on color information of each pixel constituting an image obtained by capturing an image of an inside of a lumen of a subject;
  identifying a border neighboring pixel which is a pixel existing in proximity to a border of each of the plurality of candidate regions;
  calculating feature data based on a pixel value of the border neighboring pixel; and
  distinguishing an abnormal portion region based on the feature data,
  wherein the identifying of the border neighboring pixel comprises limiting a border used for identifying the border neighboring pixel, to a part of an entire periphery of the border, and
  wherein the limiting of the border comprises:
    identifying, for each of the plurality of candidate regions, an effective pixel which is a pixel in a region effective for calculation of the feature data, from an external side region which is in a specified range outwardly from a border pixel located at the border of each of the plurality of candidate regions; and
    setting a border corresponding to the effective pixel.

15. A computer-readable recording device with an executable program stored thereon, wherein the program, upon executing by a processor, causes the processor to perform:
  detecting a plurality of candidate regions of abnormal portions based on color information of each pixel constituting an image obtained by capturing an image of an inside of a lumen of a subject;
  identifying a border neighboring pixel which is a pixel existing in proximity to a border of each of the plurality of candidate regions;
  calculating feature data based on a pixel value of the border neighboring pixel; and
  distinguishing an abnormal portion region based on the feature data,
  wherein the identifying of the border neighboring pixel comprises limiting a border used for identifying the border neighboring pixel, to a part of an entire periphery of the border, and
  wherein the limiting of the border comprises:
    identifying, for each of the plurality of candidate regions, an effective pixel which is a pixel in a region effective for calculation of the feature data, from an external side region which is in a specified range outwardly from a border pixel located at the border of each of the plurality of candidate regions; and
    setting a border corresponding to the effective pixel.

* * * * *